(12) United States Patent
Khvat et al.

(10) Patent No.: US 8,486,936 B2
(45) Date of Patent: Jul. 16, 2013

(54) ANTAGONIST OF SMOOTHENED

(75) Inventors: Alexander Khvat, San Diego, CA (US); Sergey Tkachenko, San Diego, CA (US); Ilya Okun, San Diego, CA (US); Borys Rogovoy, San Diego, CA (US); Nikolay Savchuk, Rancho Santa Fe, CA (US); John May, San Diego, CA (US); Patrick O'Connor, San Diego, CA (US); William Ripka, San Diego, CA (US); Jean-Michel Vernier, San Diego, CA (US); David Matthews, Encinitas, CA (US)

(73) Assignee: AllaChem, LLC, Carson City, NV (US)

( * ) Notice: Subject to any disclaimer, the term of this patent is extended or adjusted under 35 U.S.C. 154(b) by 223 days.

(21) Appl. No.: 12/773,656

(22) Filed: May 4, 2010

(65) Prior Publication Data

US 2011/0098291 A1    Apr. 28, 2011

Related U.S. Application Data

(60) Provisional application No. 61/175,761, filed on May 5, 2009.

(51) Int. Cl.
| | |
|---|---|
| *A61K 31/5377* | (2006.01) |
| *A61K 31/497* | (2006.01) |
| *A61K 31/437* | (2006.01) |
| *C12N 5/02* | (2006.01) |
| *C07D 471/04* | (2006.01) |
| *A61P 35/00* | (2006.01) |

(52) U.S. Cl.
USPC ............. 514/233.2; 514/253.04; 514/300; 435/375; 544/127; 544/362; 546/121

(58) Field of Classification Search
None
See application file for complete search history.

(56) References Cited

U.S. PATENT DOCUMENTS

| 7,300,929 B2 | 11/2007 | Baxter et al. | |
| 2011/0171739 A1* | 7/2011 | Kemp et al. | 436/86 |

FOREIGN PATENT DOCUMENTS

| WO | WO2006/094235 | | 8/2006 |
| WO | WO2007/064902 | | 7/2007 |
| WO | WO 2008/029152 | * | 3/2008 |
| WO | WO2008/029152 | | 3/2008 |
| WO | WO2010/034982 | | 1/2010 |

OTHER PUBLICATIONS

Berge et al.: 'Pharmaceutical Salts' J. Pharm. Sci. vol. 66, 1977, pp. 1-19.
Douard et al., "Sonic Hedgehog-dependent proliferation in a series of patients with colorectal cancer", Surgery 139, 665-670 (2006).
Huang et al., "Activation of the hedgehog pathway in human hepatocellular carcinomas", Carcinogenesis 27, 1334-1340 (2006).
Kinto N.; Iwamoto M.; Enomoto-Iwamoto M.; Noji S.; Ohuchi H.; Yoshioka H.; Kataoka H.; Wada Y.; Yuhao G.; Takahashi H.E.: 'Fibroblasts expressing Sonic hedgehog induce osteoblast differentiation and ectopic bone formation' FEBS Lett. vol. 404, No. 2-3, 1997, pp. 319-323.
Ma et al., "Frequent activation of the hedgehog pathway in advanced gastric adenocarcinomas", Carcinogenesis 26, 1698-1705 (2005).
Sanchez et al., "Inhibition of prostate cancer proliferation by interference with Sonic Hedgehog-GLI1 signaling", PNAS 101, 12561-12566 (2004).
Spinella-Jaegle S.; Rawadi G.; Kawai S.; Gallea S.; Faucheu C.; Mollat P.; Courtois B.; Bergaud B.; Ramez V.; Blanchet A.M.: 'Sonic hedgehog increases the commitment of pluripotent mesenchymal cells into the osteoblastic lineage and abolishes adipocytic differentiation' J. Cell Sci. vol. 114, 2001, pp. 2085-2094.
Thayer et al., "Hedgehog is an early and late mediator of pancreatic cancer tumorigenesis", Nature 425, 851-855(2003).
Watkins et al., "Hedgehog signalling within airway epithelial progenitors and in small-cell lung cancer", Nature 422, 313-317 (2003).
Zhu & MA, "Synthesis of Aryl Sulfones via L-Proline-Promoted CuI-Catalyzed Coupling Reaction of Aryl Halides with Sulfinic Acid Salts", J Org. Chem., 2005, 70 (7), 2696-2700.

* cited by examiner

*Primary Examiner* — Dennis Heyer
(74) *Attorney, Agent, or Firm* — Sughrue Mion, PLLC

(57) ABSTRACT

Described herein are compounds, pharmaceutical compositions and methods for the inhibition of Hedgehog signaling. Said compounds, pharmaceutical compositions and methods have utility in the treatment of human and veterinary diseases and disorders.

17 Claims, 1 Drawing Sheet

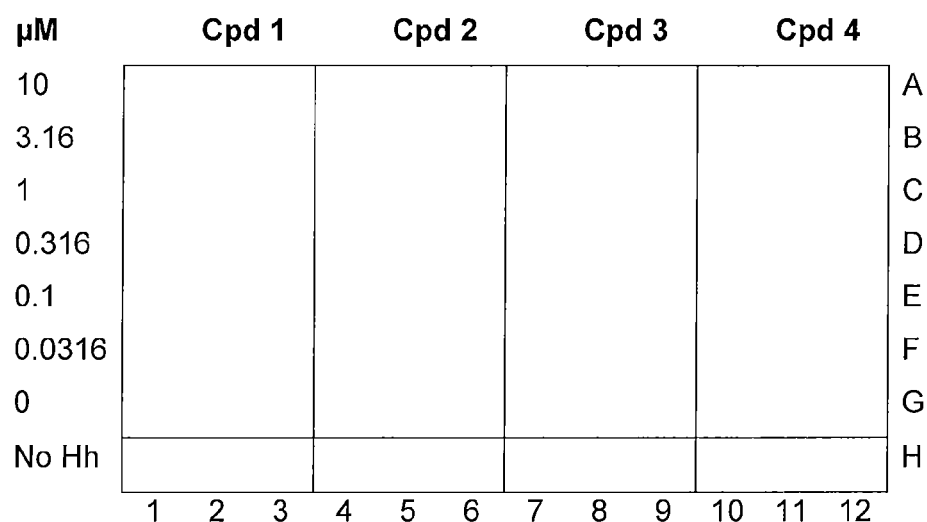
Sample Assay Plate Layout

ANTAGONIST OF SMOOTHENED

CROSS REFERENCE TO RELATED APPLICATIONS

This application claims priority to U.S. Provisional Application No. 61/175,761, filed May 5, 2009, which is incorporated by reference in its entirety.

BACKGROUND OF THE INVENTION

Since the late 1990's, scientists have unraveled several of the complex processes by which normal cells become cancer cells and developed a deeper knowledge of the heterogeneous nature of tumors. The mutational events which result in aberrant growth factor signaling in bulk tumor cells has led to the theory of "oncogene addiction", that ascribes cancer cell proliferation and survival to a dependence upon the activation of certain pathways or on the activity of oncogenic proteins within these pathways. More recently, researchers have found small populations of tumor cells with "stem cell" like characteristics, commonly referred to as cancer stem cells, within human primary tumor samples. These newly described cancer stem cells replicate more slowly, are more resistant to conventional chemotherapy, and their survival appears to be a major contributor to tumor re-growth following surgery and/or chemotherapy. In contrast to bulk tumor cells, cancer stem cells appear to be more reliant on embryonic pathways for their proliferation and survival traits.

The Hedgehog (Hh) Pathway: Several key signaling pathways (e.g. Hedgehog, Notch, Wnt) are involved in most processes essential to the normal development of an embryo. The Hedgehog pathway was initially discovered in Drosophila by Dr. Eric Wieschaus and Dr. Christiane Nusslein-Volhard, and is a major regulator for cell differentiation, tissue polarity and cell proliferation. The Hedgehog pathway plays a crucial role in tumorigenesis when reactivated in adult tissues through either mutation or other mechanisms. The Hedgehog pathway is an important driver of tumorigenesis in at least one-third of all types of cancer.

Oncogenic mutations in the Hedgehog pathway have been found in basal cell carcinoma and medulloblastoma, and Hh over expression is associated with at least pancreatic, colon, gastric, liver and prostate cancer. The estimated incidence of cancers with ligand dependent activation of Hh in the US is >200,000 cases annually and approximately 10-fold higher worldwide.

| Hh Pathway Over Expression in Solid Tumors | | | |
|---|---|---|---|
| Tumor | 2008 New US Cases (Deaths) | Hh Pathway Expression (% Total) | References |
| Colon | 108,070 (49,960) | 92,940 (86%) | Douard et al, Surgery 136, 665-670 (2006) |
| Lung | 215,020 (161,840) | 53,755 (25%-50%) | Watkins et al, Nature 422, 313-317 (2003) |
| Pancreas | 37,680 (34,290) | 18,840 (50%) | Thayer et al, Nature 425, 851-855. (2003) |
| Gastric | 21,500 (10,880) | 13,760 (64%) | Ma et al, Carcinogenesis 26, 1698-1705 (2005) |
| Hepatocellular | 21,370 (18,410) | 10,685 (50%) | Huang et al Carcinogenesis 27, 1334-1340 (2006) |
| Prostate | 186,320 (28,660) | 55,896 (30%) | Sanchez et al, PNAS 101, 12561-12566 (2004) |
| Total | 589,960 | 245,876 (41%) | |

More is becoming known about the role of cancer stem cells in the recurrence and spread of cancer. Control of the self-renewal and differentiation processes in cancer stems cells is thought to be regulated by embryonic pathways including Hedgehog. Growing evidence suggests that these pathways are deregulated in several cases, leading to abnormal cellular expansion and the formation of cancer.

Human Sonic Hedgehog protein (SHh) is synthesized as a 45 kDa precursor protein that undergoes autocleavage to yield a 20 kDa fragment that is responsible for normal Hedgehog pathway signaling. At the cell surface that Hedgehog signal is thought to be relayed through the 12 transmembrane domain protein, Patched (Ptc) and the 7 transmembrane domain protein, Smoothened (Smo). In normal adult cells, Ptc serves as a negative regulatory of Smo activity. The binding of SHh to Ptc inhibits the normal inhibitory effect of Ptc on Smo allowing Smo to transduce the SHh signal across the plasma membrane. The signal cascade initiated by Smo results in the activation of Gli transcription factors that migrate to the nucleus where they control target transcription factors effecting cell growth and differentiation in embryonic cells and where uncontrolled activation in adult cells is associated with malignancies.

SUMMARY OF THE INVENTION

The present invention provides compounds and methods relating to the Hedgehog signaling pathway, in which the pathway is regulated such that aberrant growth states are partially or completely controlled, reversed, or inhibited. The structures of the compounds are provided, along with their synthetic preparations, methods of use, and formulations.

BRIEF DESCRIPTION OF THE DRAWINGS

FIG. 1 shows a sample assay plate layout for four compounds.

DETAILED DESCRIPTION OF THE INVENTION

Imidazopyridine Smoothened Antagonists

One embodiment provides a compound having the structure of Formula (I):

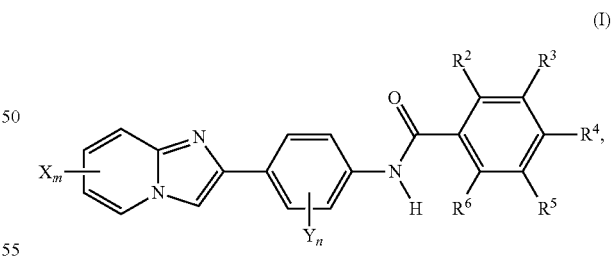

(I)

or a stereoisomer, hydrate, solvate or pharmaceutically acceptable salt thereof, wherein:
m is 0, 1 or 2; n is 0, 1, or 2;
X is $C_1$-$C_3$ alkyl, halogen or CN;
Y is $C_1$-$C_3$ alkyl, halogen or CN;
$R^2$ is selected from the group consisting of halogen, —CN, alkyl, —O-aryl, —O-heteroaryl, —$CH_2$-aryl, —$CH_2$-heteroaryl, —NH-aryl, —$SO_2$-aryl, —NH-heteroaryl, —NH-alkyl, —$CH_2$—NH-alkyl, —$CH_2$—N(alkyl)$_2$, —$CH_2$-(N-linked heterocycle), —$CH_2$-(C-linked heterocycle), N-linked heterocycle, and C-linked heterocycle;

$R^3$, $R^5$, and $R^6$ are independently selected from the group consisting of hydrogen, halogen, —CN, alkyl, aryl, heteroaryl, C-linked heterocycle, —O-alkyl, —O-aryl, —O-heteroaryl, N-linked heterocycle, —NHalkyl, —N(alkyl)$_2$, —NHaryl, —NH-heteroaryl, —CO$_2$H, —CO$_2$alkyl, —SO$_2$alkyl, —SO$_2$NH$_2$, —SO$_2$NHalkyl, —SO$_2$N(alkyl)$_2$, —NHSO$_2$alkyl, —NHSO$_2$aryl, —NHCONHalkyl, —NHCON(alkyl)$_2$, —N(alkyl)CONH$_2$, —N(alkyl)CONH(alkyl), and —N(alkyl)CON(alkyl)$_2$; and $R^4$ is selected from the group consisting of alkoxy, —CN, —SO$_2$-alkyl, —SO$_2$NH$_2$, —SO$_2$NH-alkyl, —NHSO$_2$-alkyl, —NHSO$_2$-aryl, —NHCO-alkyl, —NHCO-aryl, —NHCONH-alkyl, —NHCONH-aryl, —CONH$_2$, —CONH-alkyl, —CONH-aryl, —CON(alkyl)$_2$, —CON(aryl)$_2$, —CO$_2$H, and —CO$_2$alkyl.

Another embodiment provides the compound of Formula (I), wherein n is 0 or 1, and m is 0 or 1. Another embodiment provides the compound of Formula (I), wherein X is $C_1$-$C_3$ alkyl.

Another embodiment provides the compound of Formula (II):

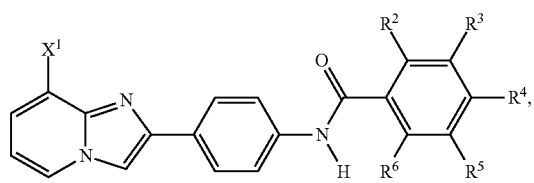

or a stereoisomer, hydrate, solvate or pharmaceutically acceptable salt thereof, wherein:

$X^1$ is hydrogen or $C_1$-$C_3$ alkyl;

$R^2$ is selected from the group consisting of halogen, —CN, alkyl, —O-aryl, —O-heteroaryl, —CH$_2$-aryl, —CH$_2$-heteroaryl, —NH-aryl, —NH-heteroaryl, —NH-alkyl, —CH$_2$—NH-alkyl, —CH$_2$—N(alkyl)$_2$, —CH$_2$-(N-linked heterocycle), —CH$_2$-(C-linked heterocycle), N-linked heterocycle, and C-linked heterocycle;

$R^3$, $R^5$, and $R^6$ are independently selected from the group consisting of hydrogen, halogen, —CN, alkyl, aryl, heteroaryl, C-linked heterocycle, —O-alkyl, —O-aryl, —O-heteroaryl, N-linked heterocycle, —NHalkyl, —N(alkyl)$_2$, —NHaryl, —NH-heteroaryl, —CO$_2$H, —CO$_2$alkyl, —SO$_2$alkyl, —SO$_2$NH$_2$, —SO$_2$NHalkyl, —SO$_2$N(alkyl)$_2$, —NHSO$_2$alkyl, —NHSO$_2$aryl, —NHCONHalkyl, —NHCON(alkyl)$_2$, —N(alkyl)CONH$_2$, —N(alkyl)CONH(alkyl), and —N(alkyl)CON(alkyl)$_2$; and $R^4$ is selected from the group consisting of alkoxy, —CN, —SO$_2$-alkyl, —SO$_2$NH$_2$, —SO$_2$NH-alkyl, —NHSO$_2$-alkyl, —NHSO$_2$-aryl, —NHCO-alkyl, —NHCO-aryl, —NHCONH-alkyl, —NHCONH-aryl, —CONH$_2$, —CONH-alkyl, —CONH-aryl, —CON(alkyl)$_2$, —CON(aryl)$_2$, —CO$_2$H, and —CO$_2$alkyl.

Another embodiment provides the compound of Formula (II), wherein $R^2$ is selected from the group consisting of halogen, —CN, alkyl, —O-aryl, —O-heteroaryl, —CH$_2$-aryl, —CH$_2$-heteroaryl, —NH-aryl, —NH-heteroaryl, —NH-alkyl, —CH$_2$—NH-alkyl, —CH$_2$—N(alkyl)$_2$, —CH$_2$-(N-linked heterocycle), —CH$_2$-(C-linked heterocycle), N-linked heterocycle, and C-linked heterocycle;

$R^3$, $R^5$, and $R^6$ are independently selected from the group consisting of hydrogen, halogen, —CN, alkyl, aryl, heteroaryl, —O-alkyl, —CO$_2$H, —SO$_2$alkyl, and —SO$_2$NH$_2$.

Another embodiment provides the compound of Formula (II), wherein $R^4$ is selected from the group consisting of alkoxy, —CN, —SO$_2$-alkyl, —SO$_2$NH$_2$, —NHSO$_2$-alkyl, —CONH$_2$, —CONH-alkyl, and —CO$_2$H.

Another embodiment provides the compound of Formula (II), wherein $R^3$, $R^5$, and $R^6$ are independently selected from the group consisting of hydrogen, halogen, —CN, alkyl, —O-alkyl, —CO$_2$H, —SO$_2$alkyl, and —SO$_2$NH$_2$; and $R^4$ is selected from the group consisting of alkoxy, —CN, —SO$_2$-alkyl, —SO$_2$NH$_2$, —NHSO$_2$-alkyl, —CONH$_2$, —CONH-alkyl, and —CO$_2$H.

Another embodiment provides the compound of Formula (II), wherein $X^1$ is methyl, ethyl, or trifluoromethyl. Another embodiment provides the compound of Formula (II), wherein $X^1$ is hydrogen.

Another embodiment provides the compound of Formula (II), wherein $R^3$, $R^5$, and $R^6$ are hydrogen. Another embodiment provides the compound of Formula (II), wherein $R^4$ is selected from alkoxy or —SO$_2$-alkyl.

Another embodiment provides the compound of Formula (II), wherein $R^2$ is selected from the group consisting of F, Cl, Br, —CN,

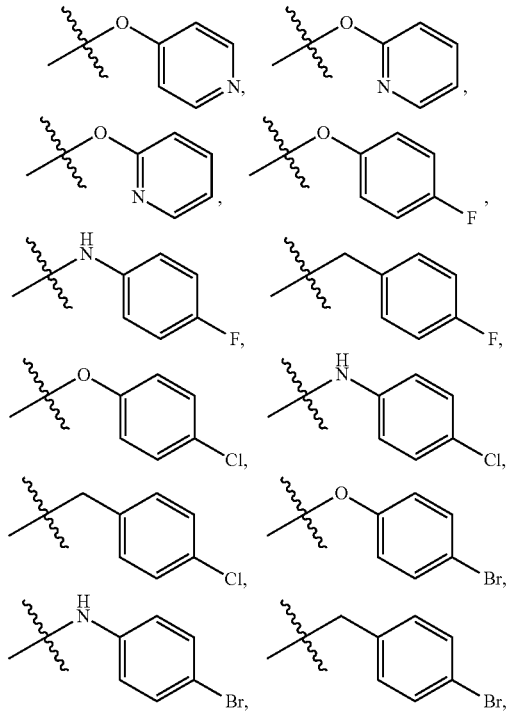

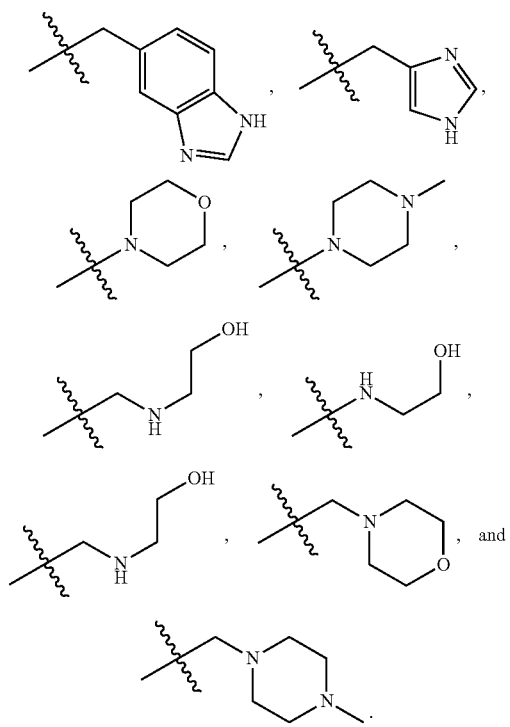

Another embodiment provides the compound of Formula (II), wherein $R^3$, $R^5$, and $R^6$ are hydrogen. Another embodiment provides the compound of Formula (II), wherein $R^4$ is selected from alkoxy or —$SO_2$-alkyl. Another embodiment provides the compound of Formula (II), wherein $R^4$ is —$OCH_3$ or —$SO_2CH_3$. Another embodiment provides the compound of Formula (II), wherein $X^1$ is methyl, ethyl, or trifluoromethyl. Another embodiment provides the compound of Formula (II), wherein $X^1$ is hydrogen.

One embodiment provides a compound selected from the group consisting of:

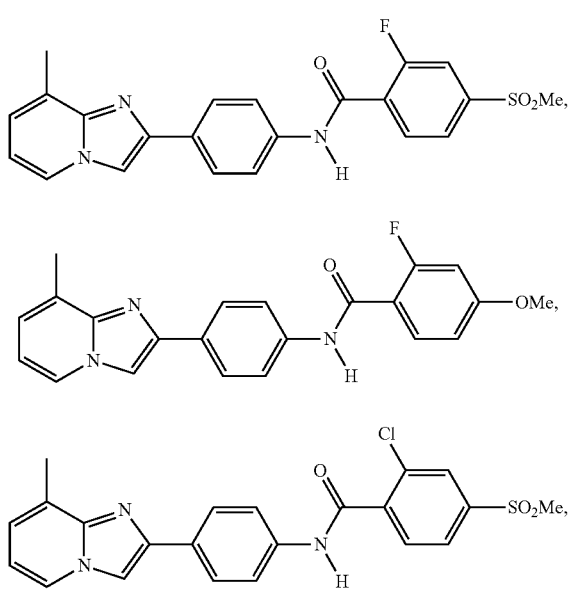

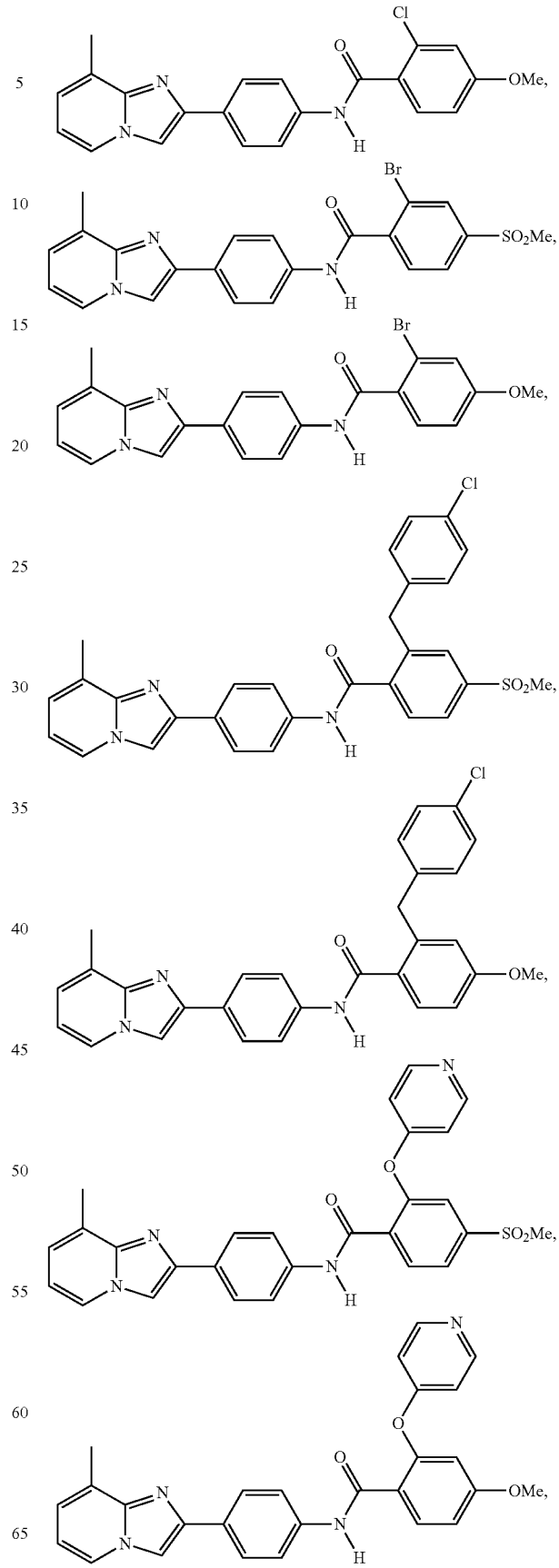

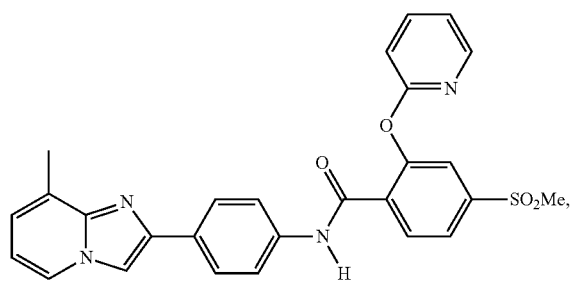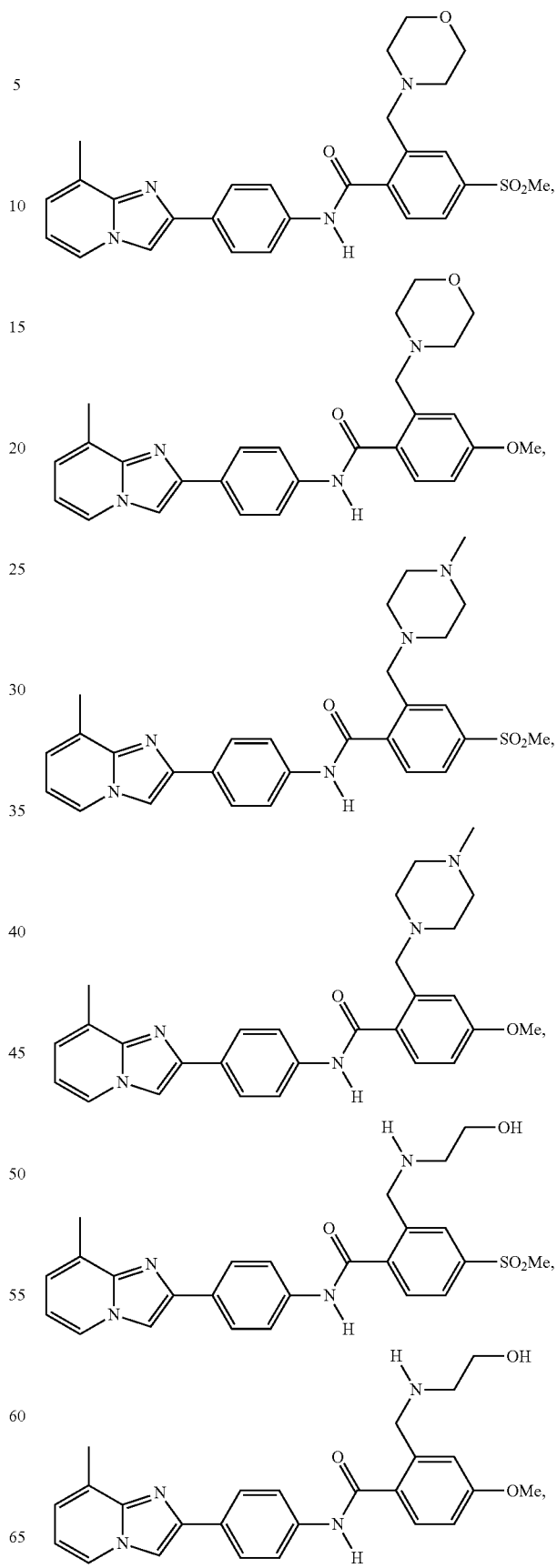

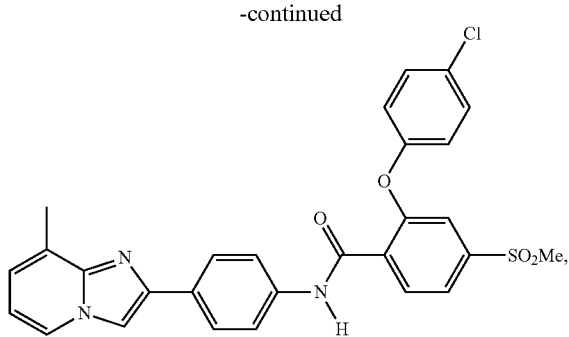

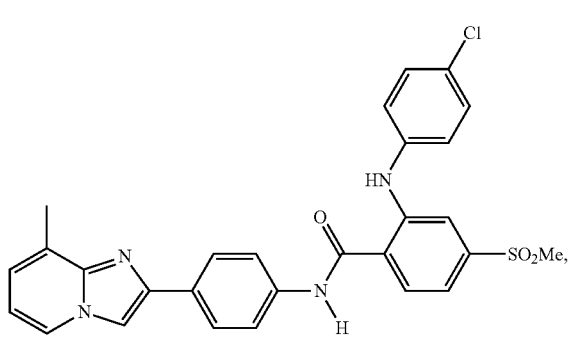

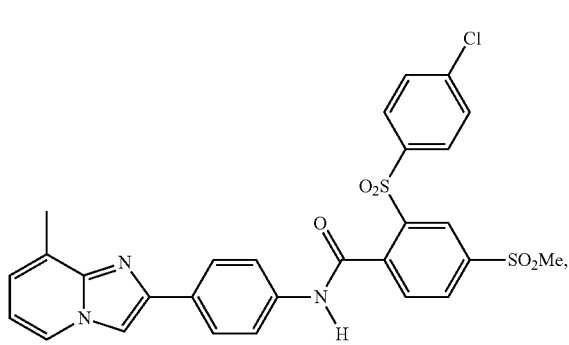

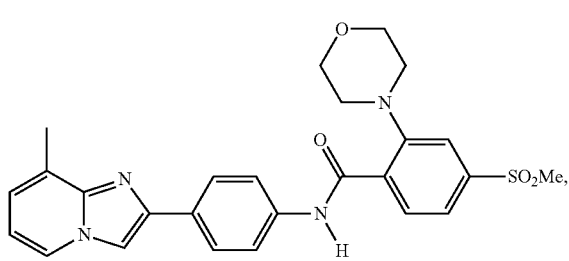

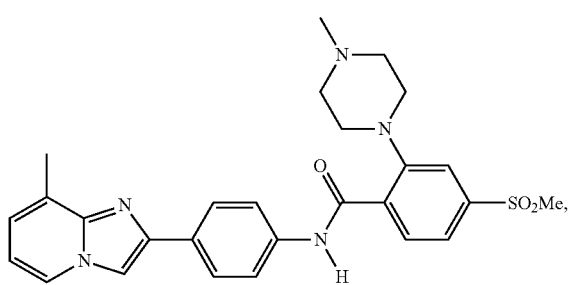

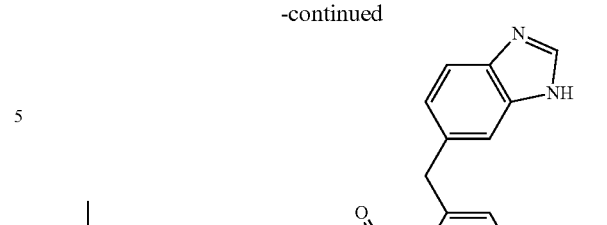

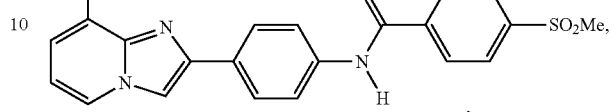

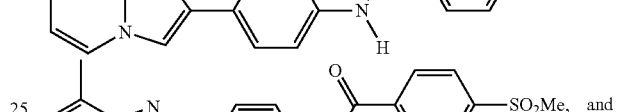

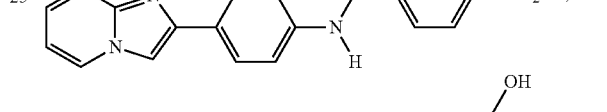

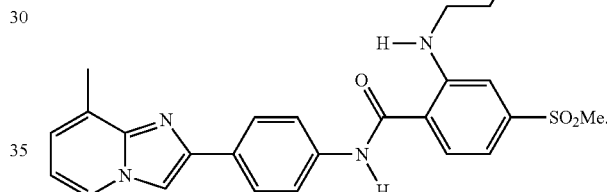

One embodiment provides a pharmaceutical composition comprising a compound of Formula (I) or (II), or a stereoisomer, hydrate, solvate or pharmaceutically acceptable salt thereof, and at least one pharmaceutically acceptable excipient.

One embodiment provides a compound having the structure of Formula (IV):

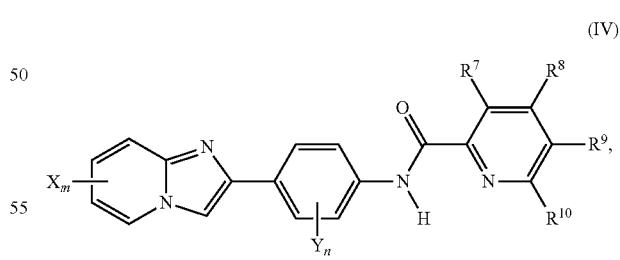

or a stereoisomer, hydrate, solvate or pharmaceutically acceptable salt thereof, wherein:

m is 0, 1 or 2; n is 0, 1, or 2;

X is $C_1$-$C_3$ alkyl, halogen or CN;

Y is $C_1$-$C_3$ alkyl, halogen or CN;

$R^7$ is selected from the group consisting of hydrogen, halogen, —CN, alkyl, —O-aryl, —O-heteroaryl, —$CH_2$-aryl, —$CH_2$-heteroaryl, —NH-aryl, —NH-heteroaryl, —NH-alkyl, —$CH_2$—NH-alkyl, —$CH_2$—N(alkyl)$_2$, —$CH_2$-(N- linked heterocycle), —CH₂-(C-linked heterocycle), N-linked heterocycle, and C-linked heterocycle;

R⁸ and R¹⁰ are independently selected from the group consisting of hydrogen, halogen, —CN, alkyl, aryl, heteroaryl, C-linked heterocycle, —O-alkyl, —O-aryl, —O-heteroaryl, N-linked heterocycle, —NHalkyl, —N(alkyl)₂, —NHaryl, —NH-heteroaryl, —CO₂H, —CO₂alkyl, —SO₂alkyl, —SO₂NH₂, —SO₂NHalkyl, —SO₂N(alkyl)₂, —NHSO₂alkyl, —NHSO₂aryl, —NHCONHalkyl, —NHCON(alkyl)₂, —N(alkyl)CONH₂, —N(alkyl)CONH(alkyl), and —N(alkyl)CON(alkyl)₂; and R⁹ is selected from the group consisting of alkoxy, —CN, —SO₂-alkyl, —SO₂NH₂, —SO₂NH-alkyl, —NHSO₂-alkyl, —NHSO₂-aryl, —NHCO-alkyl, —NHCO-aryl, —NHCONH-alkyl, —NHCONH-aryl, —CONH₂, —CONH-alkyl, —CONH-aryl, —CON(alkyl)₂, —CON(aryl)₂, —CO₂H, and —CO₂alkyl.

Another embodiment provides the compound of Formula (IV), wherein n is 0 or 1, and m is 0 or 1.

Another embodiment provides the compound of Formula (IV), wherein X is C₁-C₃ alkyl.

Another embodiment provides the compound of Formula (IV), having the structure of Formula (V):

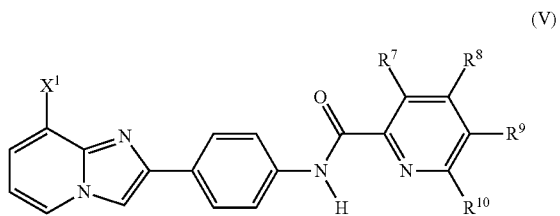

(V)

or a stereoisomer, hydrate, solvate or pharmaceutically acceptable salt thereof, wherein:

X¹ is hydrogen or C₁-C₃ alkyl;

R⁷ is selected from the group consisting of halogen, alkyl, —O-aryl, —O-heteroaryl, —CH₂-aryl, —CH₂-heteroaryl, —NH-aryl, —NH-heteroaryl, —NH-alkyl, —CH₂—NH-alkyl, —CH₂—N(alkyl)₂, —CH₂-(N-linked heterocycle), —CH₂-(C-linked heterocycle), N-linked heterocycle, and C-linked heterocycle;

R⁸ and R¹⁰ are independently selected from the group consisting of hydrogen, halogen, —CN, alkyl, aryl, heteroaryl, C-linked heterocycle, —O-alkyl, —O-aryl, —O-heteroaryl, N-linked heterocycle, —NHalkyl, —N(alkyl)₂, —NHaryl, —NH-heteroaryl, —CO₂H, —CO₂alkyl, —SO₂alkyl, —SO₂NH₂, —SO₂NHalkyl, —SO₂N(alkyl)₂, —NHSO₂alkyl, —NHSO₂aryl, —NHCONHalkyl, —NHCON(alkyl)₂, —N(alkyl)CONH₂, —N(alkyl)CONH(alkyl), and —N(alkyl)CON(alkyl)₂; and R⁹ is selected from the group consisting of alkoxy, —CN, —SO₂-alkyl, —SO₂NH₂, —SO₂NH-alkyl, —NHSO₂-alkyl, —NHSO₂-aryl, —NHCO-alkyl, —NHCO-aryl, —NHCONH-alkyl, —NHCONH-aryl, —CONH₂, —CONH-alkyl, —CONH-aryl, —CON(alkyl)₂, —CON(aryl)₂, —CO₂H, and —CO₂alkyl.

Another embodiment provides the compound of Formula (V), wherein

R⁷ is selected from the group consisting of halogen, alkyl, —O-aryl, —O-heteroaryl, —CH₂-aryl, —CH₂-heteroaryl, —NH-aryl, —NH-heteroaryl, —NH-alkyl, —CH₂—NH-alkyl, —CH₂—N(alkyl)₂, —CH₂-(N-linked heterocycle), —CH₂-(C-linked heterocycle), N-linked heterocycle, and C-linked heterocycle;

R⁸ and R¹⁰ are independently selected from the group consisting of hydrogen, halogen, —CN, alkyl, aryl, heteroaryl, —O-alkyl, —CO₂H, —SO₂alkyl, —SO₂NH₂, —SO₂NHalkyl, —SO₂N(alkyl)₂, and —NHSO₂alkyl; and R⁹ is selected from the group consisting of alkoxy, —CN, —SO₂-alkyl, —SO₂NH₂, —SO₂NH-alkyl, —NHSO₂-alkyl, —NHSO₂-aryl, —NHCO-alkyl, —NHCO-aryl, —NHCONH-alkyl, —NHCONH-aryl, —CONH₂, —CONH-alkyl, —CONH-aryl, —CON(alkyl)₂, —CON(aryl)₂, —CO₂H, and —CO₂alkyl.

Another embodiment provides the compound of Formula (IV), wherein

R⁸ and R¹⁰ are independently selected from the group consisting of hydrogen, halogen, —CN, alkyl, —O-alkyl, —CO₂H, —SO₂alkyl, and —SO₂NH₂.

Another embodiment provides the compound of Formula (IV), wherein

R⁹ is selected from the group consisting of alkoxy, —CN, —SO₂-alkyl, —SO₂NH₂, —NHSO₂-alkyl, —CONH₂, —CONH-alkyl, and —CO₂H.

Another embodiment provides the compound of Formula (IV), wherein

R⁸ and R¹⁰ are independently selected from the group consisting of hydrogen, halogen, —CN, alkyl, —O-alkyl, —CO₂H, —SO₂alkyl, and —SO₂NH₂; and R⁹ is selected from the group consisting of alkoxy, —CN, —SO₂-alkyl, —SO₂NH₂, —NHSO₂-alkyl, —CONH₂, —CONH-alkyl, and —CO₂H.

Another embodiment provides the compound of Formula (IV), wherein X is methyl, ethyl, or trifluoromethyl.

Another embodiment provides the compound of Formula (IV), wherein X is hydrogen.

Another embodiment provides the compound of Formula (IV), wherein R⁸ and R¹⁰ are hydrogen.

Another embodiment provides the compound of Formula (IV), wherein R⁹ is selected from alkoxy or —SO₂-alkyl.

Another embodiment provides the compound of Formula (IV), wherein

R⁷ is selected from the group consisting of F, Cl, Br, —CN,

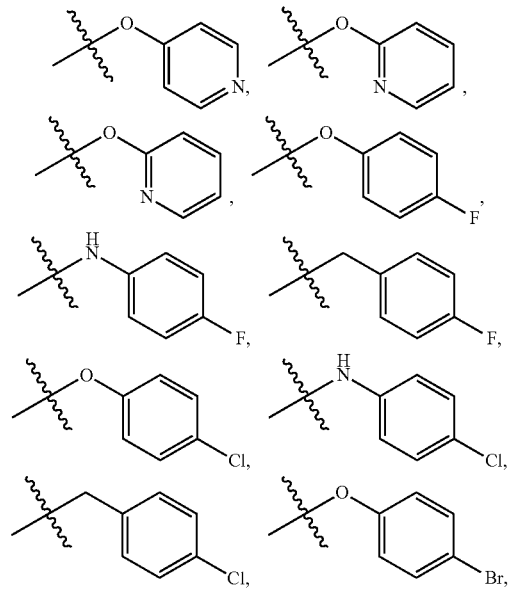

-continued

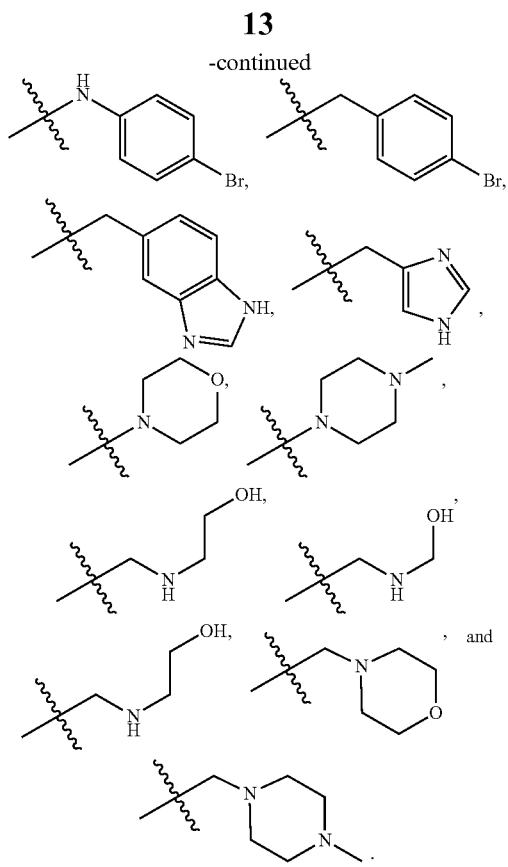

Another embodiment provides the compound of Formula (IV), wherein $R^8$ and $R^{10}$ are hydrogen.

Another embodiment provides the compound of Formula (IV), wherein $R^9$ is selected from alkoxy or —$SO_2$-alkyl.

Another embodiment provides the compound of Formula (IV), wherein $R^9$ is —$OCH_3$ or —$SO_2CH_3$.

Another embodiment provides the compound of Formula (IV), wherein $R^7$ is F, Cl, or Br.

Another embodiment provides the compound of Formula (IV), wherein X is methyl, ethyl, or trifluoromethyl.

One embodiment provides the compound selected from the group consisting of:

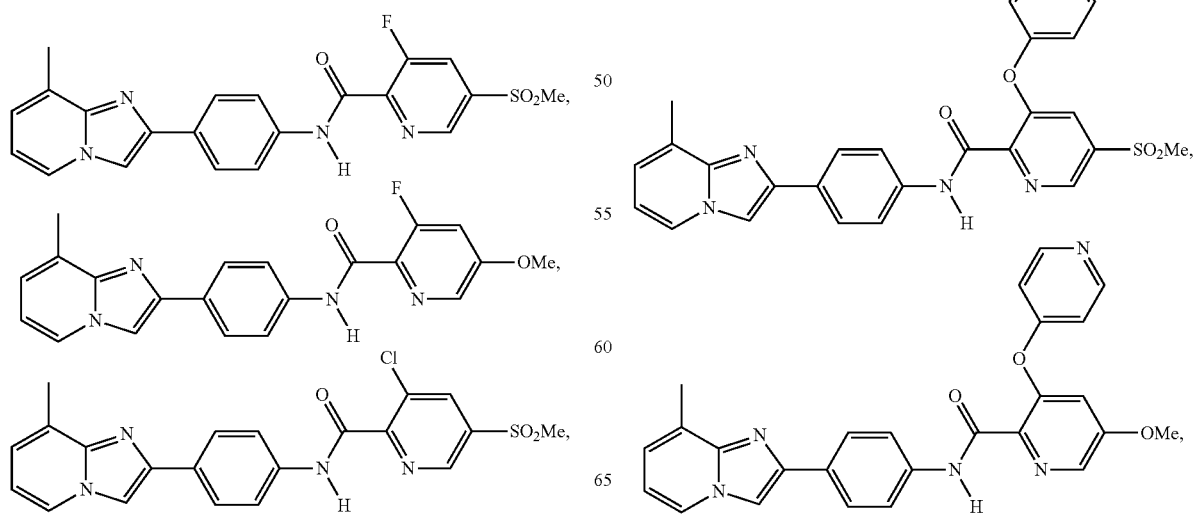

-continued

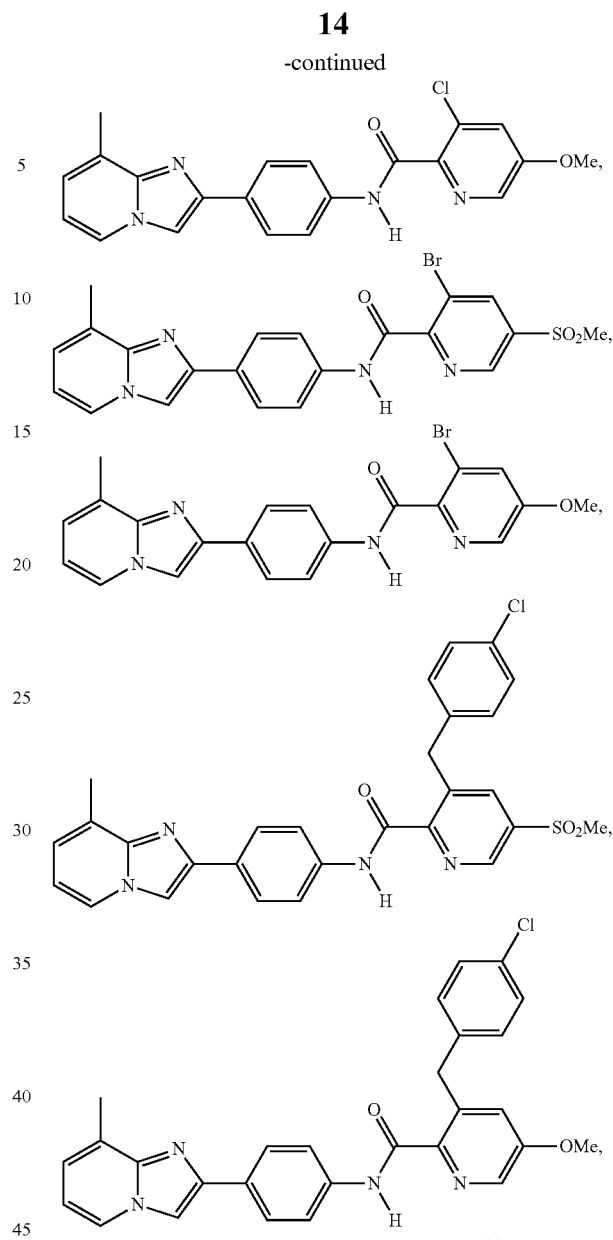

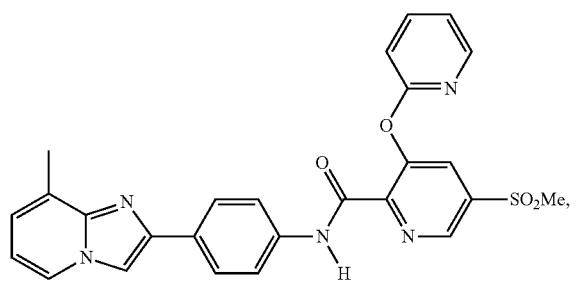
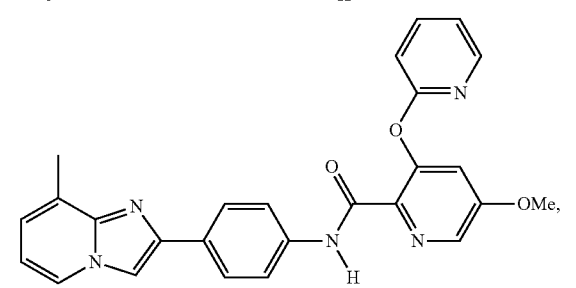
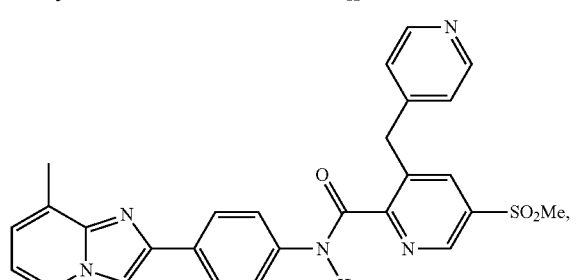
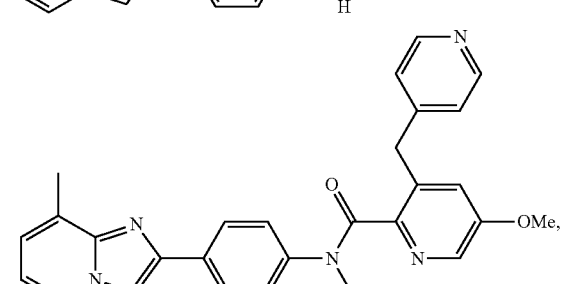
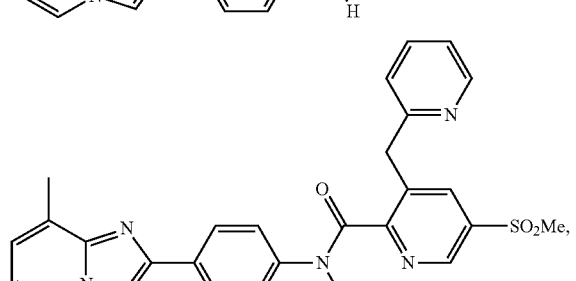
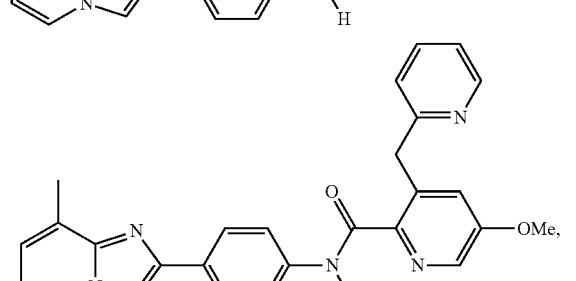

-continued

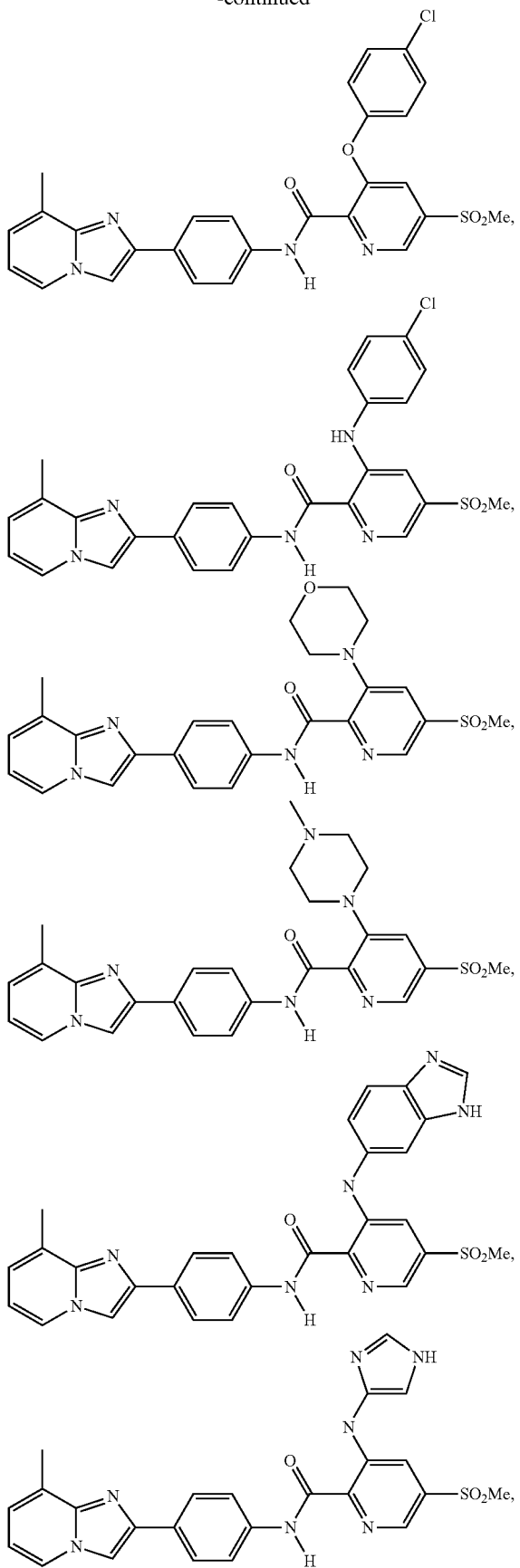

-continued

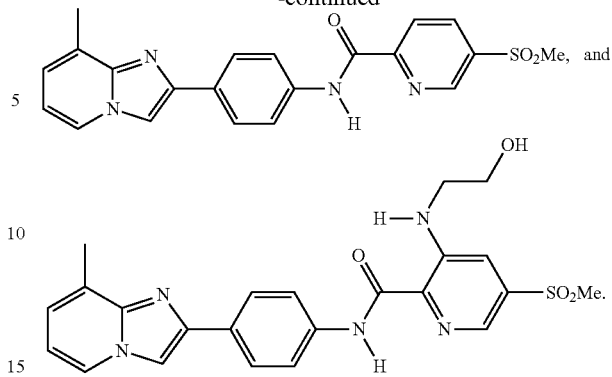

One embodiment provides a pharmaceutical composition comprising a compound of Formula (IV), or a stereoisomer, hydrate, solvate or pharmaceutically acceptable salt thereof, and at least one pharmaceutically acceptable excipient.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure.

Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "heteroatom" as used herein means an atom of any element other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF$_3$, —CN, or the like.

The term "halogen" designates —F, —Cl, —Br or —I.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

A comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to inhibit hedgehog signaling), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Methods of Inhibiting Hedgehog Signaling

One embodiment provides a method of inhibiting the Hedgehog pathway in a cell comprising contacting the cell with an inhibitory concentration of a compound of Formula (III):

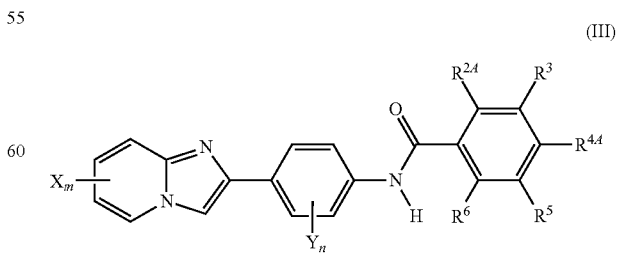

(III)

or a stereoisomer, hydrate, solvate or pharmaceutically acceptable salt thereof, wherein:

m is 1 or 2; n is 0, 1, or 2;

X is $C_1$-$C_3$ alkyl, halogen or CN;

Y is $C_1$-$C_3$ alkyl, halogen or CN;

$R^{2,4}$ is selected from the group consisting of hydrogen, —CN, halogen, alkyl, —O-aryl, —O-heteroaryl, —$CH_2$-aryl, —$CH_2$-heteroaryl, —NH-aryl, —NH-heteroaryl, —NH-alkyl, —$CH_2$—NH-alkyl, —$CH_2$—N(alkyl)$_2$, —$CH_2$-(N-linked heterocycle), —$CH_2$-(C-linked heterocycle), N-linked heterocycle, and C-linked heterocycle;

$R^3$, $R^5$, and $R^6$ are independently selected from the group consisting of hydrogen, halogen, —CN, alkyl, aryl, heteroaryl, C-linked heterocycle, —O-alkyl, —O-aryl, —O-heteroaryl, N-linked heterocycle, —NHalkyl, —N(alkyl)$_2$, —NHaryl, —NH-heteroaryl, —$CO_2H$, —$CO_2$alkyl, —$SO_2$alkyl, —$SO_2NH_2$, —$SO_2$NHalkyl, —$SO_2$N(alkyl)$_2$, —$NHSO_2$alkyl, —$NHSO_2$aryl, —NHCONHalkyl, —NHCON(alkyl)$_2$, —N(alkyl)CONH$_2$, —N(alkyl)CONH(alkyl), and —N(alkyl)CON(alkyl)$_2$; and $R^{4,4}$ is selected from the group consisting of hydrogen, halogen, alkoxy, —CN, —$SO_2$-alkyl, —$SO_2NH_2$, —$SO_2$NH-alkyl, —$NHSO_2$-alkyl, —$NHSO_2$-aryl, —NHCO-alkyl, —NHCO-aryl, —NHCONH-alkyl, —NHCONH-aryl, —$CONH_2$, —CONH-alkyl, —CONH-aryl, —CON(alkyl)$_2$, —CON(aryl)$_2$, —$CO_2H$, and —$CO_2$alkyl.

One embodiment provides a method of inhibiting the activity of smoothened protein in a cell comprising contacting the smoothened protein with an inhibitory concentration of a compound of Formula (III) or a stereoisomer, hydrate, solvate or pharmaceutically acceptable salt thereof, wherein the substituent groups are defined as above.

One embodiment provides a method of inhibiting the transcriptional activity of Gil transcription factor in a cell comprising contacting the cell with an inhibitory concentration of a compound of Formula (III) or a stereoisomer, hydrate, solvate or pharmaceutically acceptable salt thereof, wherein the substituent groups are defined as above.

One embodiment provides a method of inhibiting Gli-mediated gene transcription in a cell comprising contacting the cell with an inhibitory concentration of a compound of Formula (III) or a stereoisomer, hydrate, solvate or pharmaceutically acceptable salt thereof, wherein the substituent groups are defined as above.

One embodiment provides method of inhibiting the Hedgehog pathway in a cell comprising contacting the cell with an inhibitory concentration of a compound of Formula (IV) or a stereoisomer, hydrate, solvate or pharmaceutically acceptable salt thereof, wherein the substituent groups are defined as above.

One embodiment provides method of inhibiting the activity of smoothened protein in a cell comprising contacting the smoothened protein with an inhibitory concentration of a compound of Formula (IV) or a stereoisomer, hydrate, solvate or pharmaceutically acceptable salt thereof, wherein the substituent groups are defined as above.

One embodiment provides a method of inhibiting the transcriptional activity of Gil transcription factor in a cell comprising contacting the cell with an inhibitory concentration of a compound of Formula (IV) or a stereoisomer, hydrate, solvate or pharmaceutically acceptable salt thereof, wherein the substituent groups are defined as above.

One embodiment provides a method of inhibiting Gli-mediated gene transcription in a cell comprising contacting the cell with an inhibitory concentration of a compound of Formula (IV) or a stereoisomer, hydrate, solvate or pharmaceutically acceptable salt thereof, wherein the substituent groups are defined as above.

Another embodiment provides a method, wherein the cell is characterized by a patched loss-of-function phenotype. Another embodiment provides the method, wherein the cell is characterized by a smoothened gain-of-function phenotype. Another embodiment provides the method, wherein the cell is characterized by a constitutively active smoothened phenotype. Another embodiment provides the method, wherein the cell is characterized by expression of Gli.

Methods of Treatment

One embodiment provides a method of treating a human disease or disorder mediated by Hedgehog pathway comprising administering to a patient a therapeutically effective amount of a composition comprising a compound of Formula (III) or of Formula (IV), or a stereoisomer, hydrate, solvate or pharmaceutically acceptable salt thereof, wherein the substituent groups are defined as above.

Another embodiment provides the method of treatment, wherein the disease or disorder is a proliferative disease associated with the pathway. Another embodiment provides the method of treatment, wherein the proliferative disease is selected from colon cancer, lung cancer, pancreatic cancer, gastric cancer, prostate cancer, and hepatocellular carcinoma. Another embodiment provides the method of treatment, wherein the proliferative disease is selected from basal cell carcinoma, breast cancer, bone sarcoma, soft tissue sarcoma, chronic myeloid leukemia, acute myeloid leukemia, hematological cancer, medulloblastoma, rhabdomyosaracoma, neuroblastoma, pancreatic cancer, breast carcinoma, meningioma, glioblastoma, astrocytoma, melanoma, stomach cancer, esophageal cancer, biliary tract cancer, prostate cancer, small cell lung cancer, non-small cell lung cancer, glial cell cancer, multiple myeloma, colon cancer, neuroectodermal tumor, neuroendocrine tumor, mastocytoma and Gorlin syndrome.

Another embodiment provides the method of treatment, wherein the proliferative disease is basal cell carcinoma.

One embodiment provides the method of treatment method of treating a veterinary disease or disorder mediated by Hedgehog pathway comprising administering to a patient a therapeutically effective amount of a composition comprising a compound of Formula (III) or of Formula (IV), or a stereoisomer, hydrate, solvate or pharmaceutically acceptable salt thereof, wherein the substituent groups are defined as above.

Another embodiment provides the method of veterinary treatment, wherein the disease or disorder is a proliferative disease selected from mast cell tumors or osteosarcoma.

In another aspect, the present invention provides pharmaceutical preparations comprising hedgehog antagonists. The hedgehog antagonists for use in the subject method may be conveniently formulated for administration with a biologically acceptable medium or excipient, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog antagonist, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit Formulations".

Pharmaceutical formulations of the present invention can also include veterinary compositions, e.g., pharmaceutical preparations of the hedgehog antagonists suitable for veterinary uses, e.g., for the treatment of live stock or domestic animals, e.g., dogs.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a hedgehog antagonist at a particular target site.

The preparations of the present invention may be given orally, parenterally, topically, or rectally. They are of course given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable and/or sterile carriers and can also be administered in conjunction with other active agents. Conjunctive therapy, thus includes sequential, simultaneous and separate administration of the active compound in a way that the therapeutical effects of the first administered one is not entirely disappeared when the subsequent is administered.

While it is possible for a compound of the present invention to be administered alone, it is preferable to administer the compound as a pharmaceutical formulation (composition). The hedgehog antagonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by overcoming a ptc loss-of-function, hedgehog gain-of-function, or smoothened gain-of-function in at least a subpopulation of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, suceinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

I. Chemical Synthesis

Synthetic Schemes: Schemes 1-15 illustrate general methods for the synthesis of imidazopyridine smoothened antagonists.

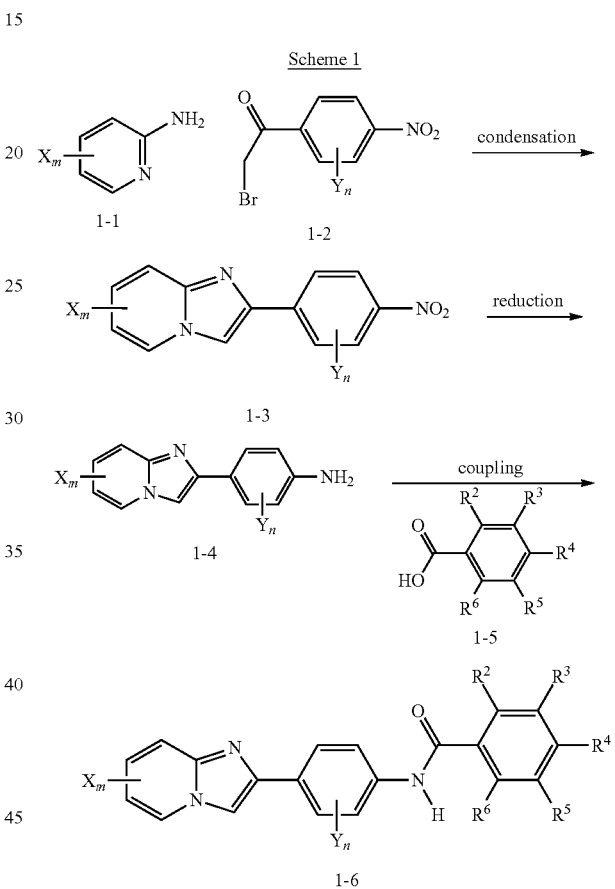

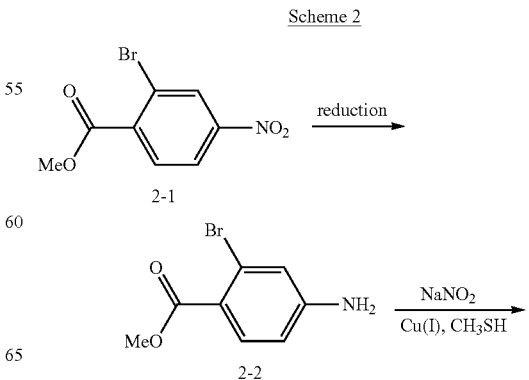

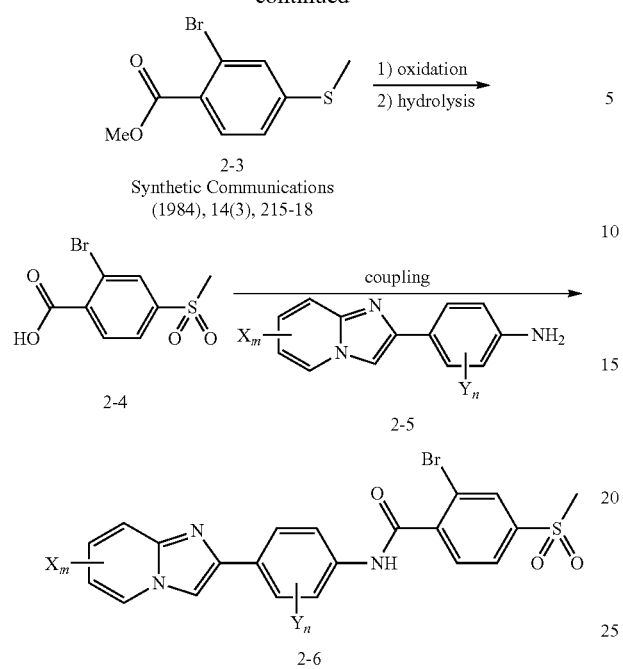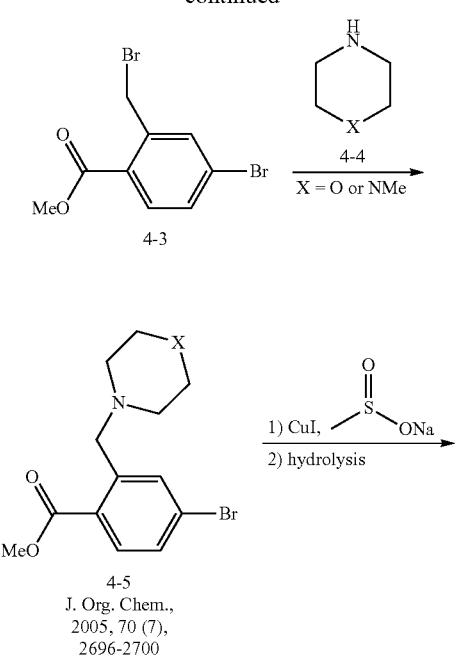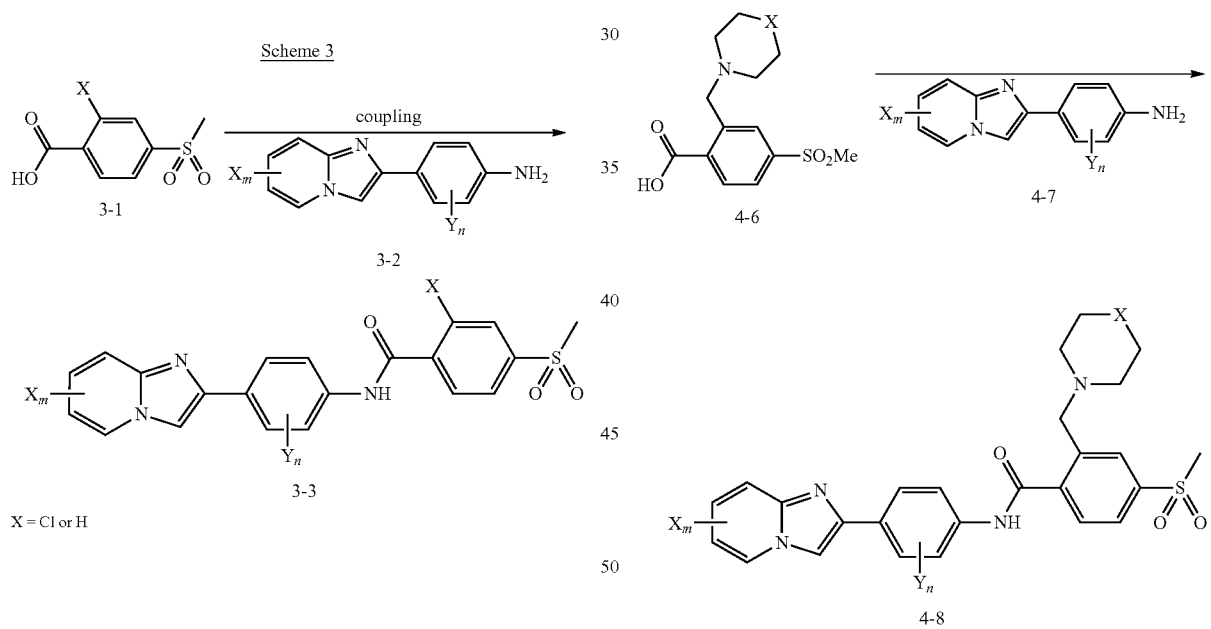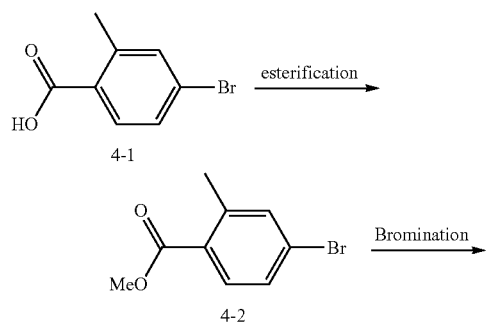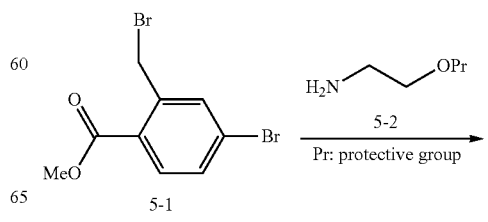

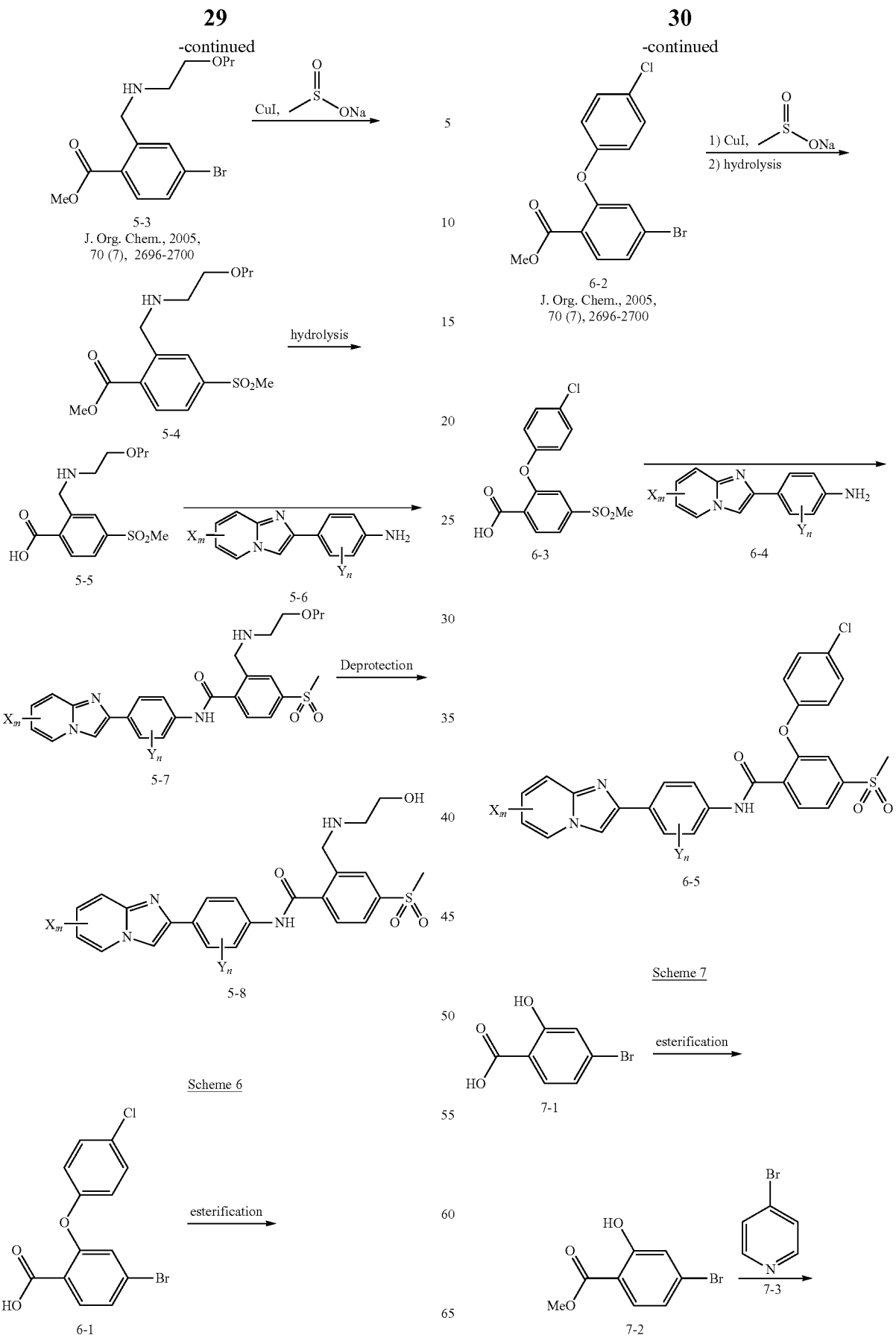

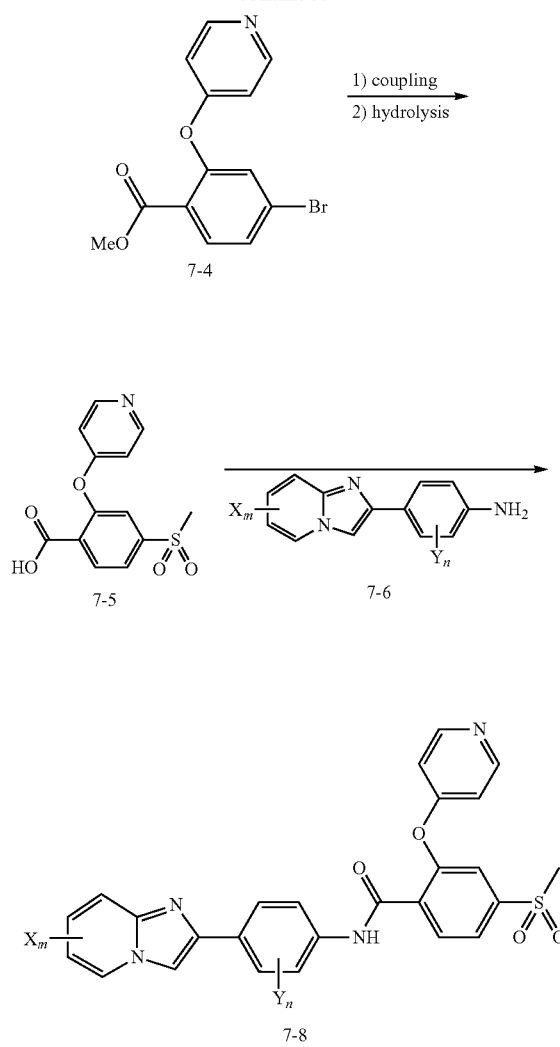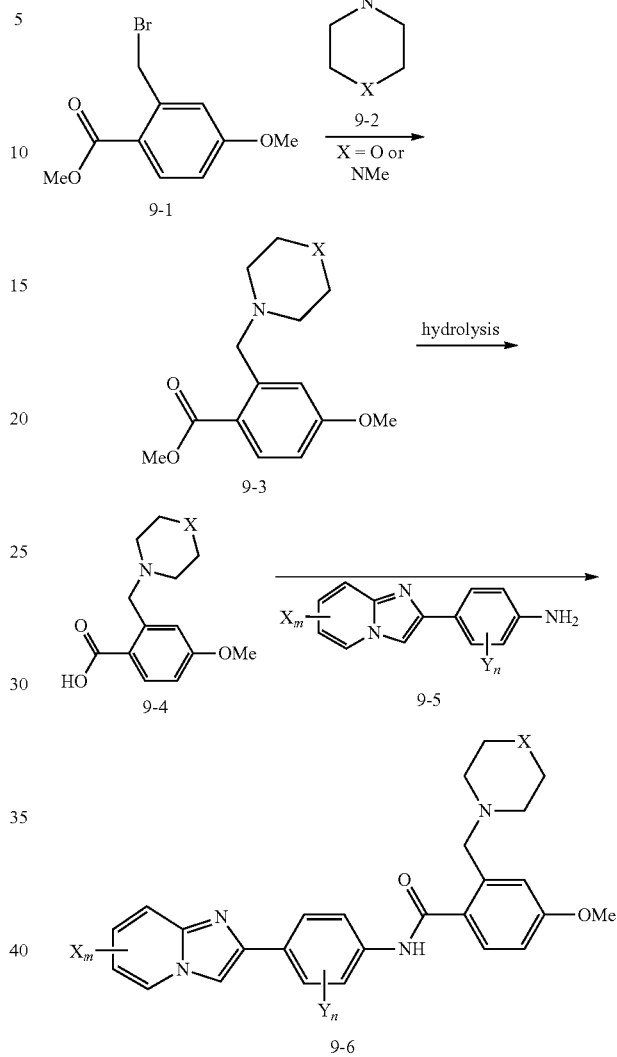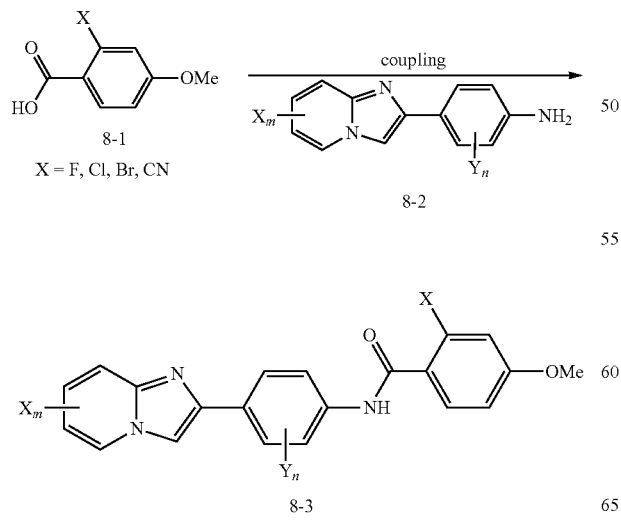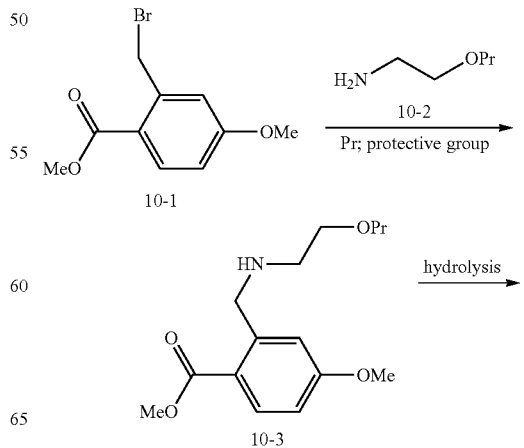

33
-continued
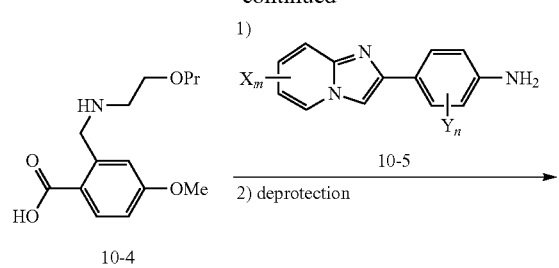
34
-continued
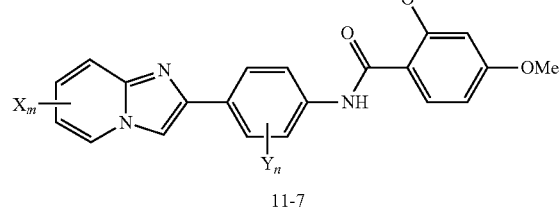
Scheme 11
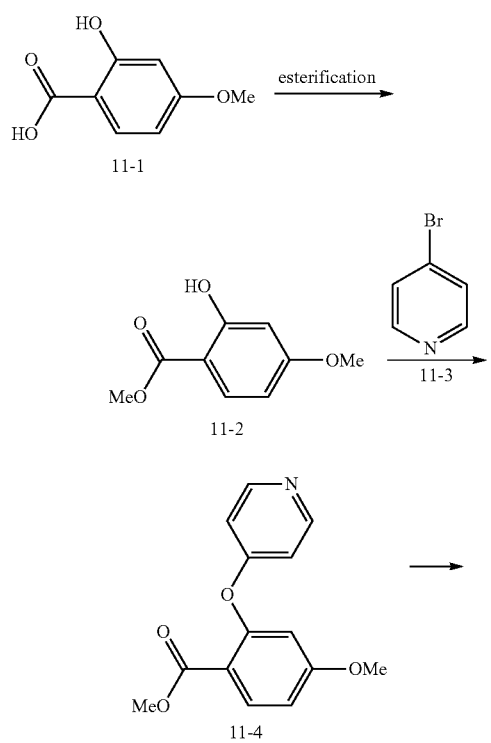
Scheme 12
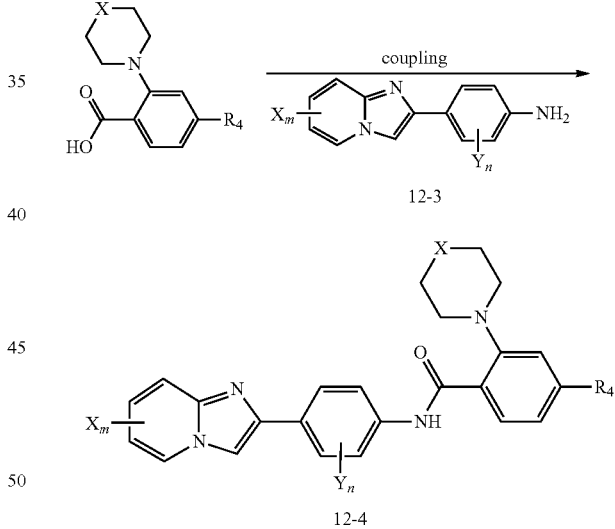
Scheme 13
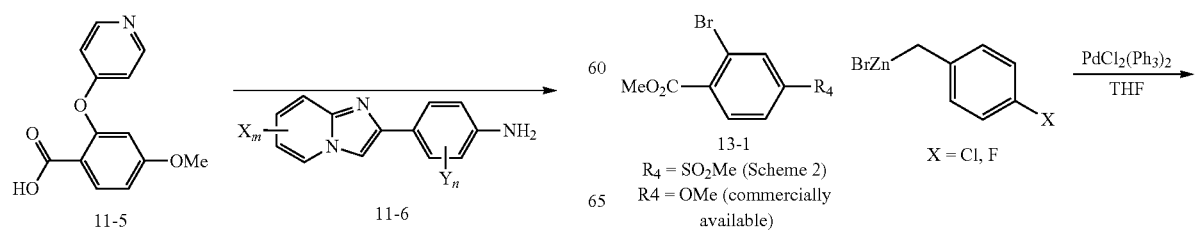

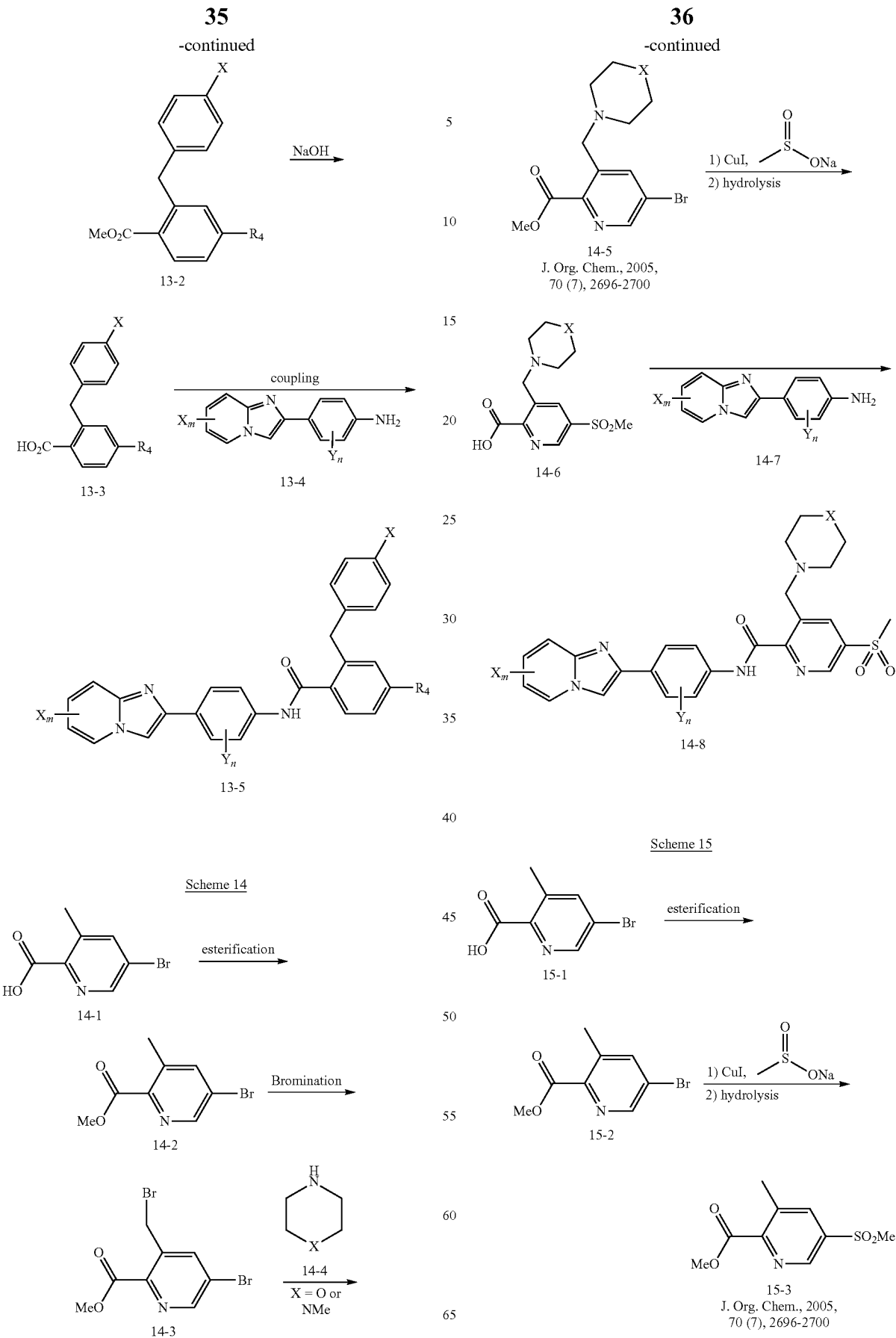

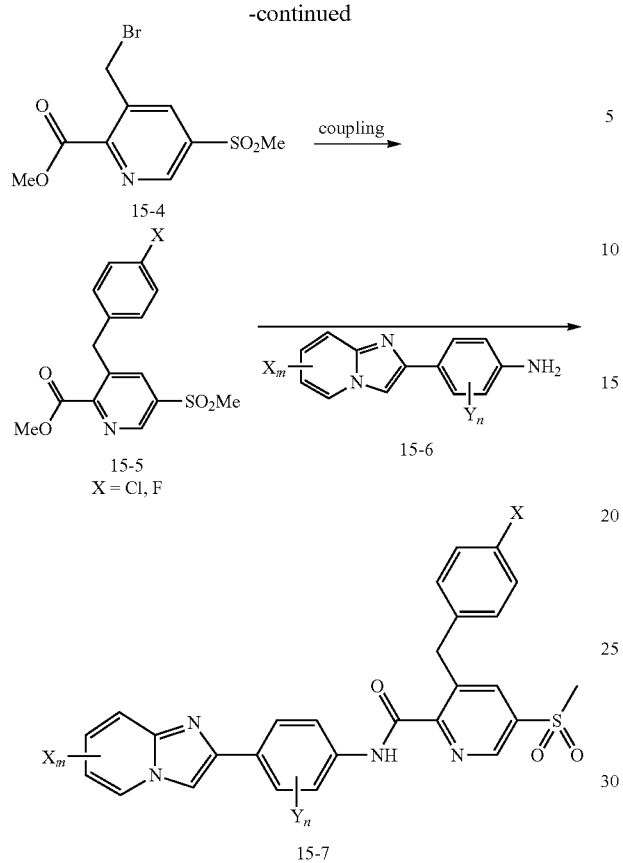

II. Biological Evaluation

Version 1—manual setup, 96-well plates, dose-response, C3H/10T1/2 cells. Aim: to determine activity of Sonic Hedgehog pathway inhibitors.

Materials

C3H/10T1/2 cells, grown in DMEM medium/10% FBS to 60-80% confluent
Assay Plates: 96-well half-area tissue culture plates Corning cat. #3697
Tested compounds as 10 mM DMSO solutions in 96-tube racks
Recombinant Human Sonic Hedgehog (C24II) protein, RDS product #1845-SH, reconstituted at 200 μg/ml in PBS.
Lysis Buffer: 10 mM Ethanolamine Buffer (pH 8.0), 0.2% Triton-X100, supplemented 1:100 with Protease Inhibitor Cocktail (EMD Bioscience product #539134).
CSPD Alkaline Phosphatase Substrate with Emerald-II (Applied Biosystems product #T2212).
Prepare 1 Assay plate for every 4 compounds (see FIG. 1):
 1. Harvest C3H/10T1/2 cells with TrypLE Express solution according to a regular cell subculture protocol
 2. Count the cells and calculate dilution necessary to obtain cell suspension at $5\times10^3$ cells per 40 μl ($1.25\times10^6$ cells/ml)
 3. Dilute cells with DMEM/10% FBS and distribute at 40 μl/well
 4. Place the plate(s) into the incubator and allow cells to attach for 3-5 hours Prepare dilution plate:
 1. Designate 1 column for each compound
 2. Add 99 μl of DMEM/10% FBS to the wells in row A and 50 μl to the wells in rows B-H
 3. Add 1 μl of compound DMSO stocks to the wells in row A, mix, change the tip
 4. Transfer 23.1 of compound solutions in row A to the wells in row B, mix, change the tip
 5. Continue serial dilutions through row F, do not transfer further. Row G is a "no compound" positive control; row H is a "no Hedgehog" negative control
Add 5 μl/well of 10× compound dilutions from dilution plate to the corresponding wells in assay plates (see assay plate layout). Use 125 μl automatic repeating pipettor.
Place plates into incubator for 20-30 min.
Prepare 3 μg/ml 10× solution of Sonic Hedgehog (C24II) protein (Hh) in DMEM/10% FBS:
 1. Calculate total volume needed as 500 μl per full plate or 125 μl per each compound tested
 2. Add 1.5 μl of Hh stock solution (200 μg/ml in PBS) per each 98.5 μl of medium
Add 5 μl/well of 10× Hh solution to the wells in rows A-G, add 5 μl/well of medium to the wells in row H (see assay plate layout). Use 125 μl automatic repeating pipettor.
Place plates into incubator for 3 days.
Wash cells on plate: aspirate medium, add 100 μl/well of PBS or HBSS and aspirate again.
Add 20 μl/well of lysis buffer and incubate for 15 min. at room temperature on a shaker platform.
Transfer 7.5 μl/well of cell lysate into white opaque plates and add 45 μl/well of CSPD Alkaline Phosphatase substrate.
Cover from light and incubate for 45 min. at room temperature on a shaker platform.
Read the plate(s) on Wallac VictorV reader using Luminescence (0.1 s) protocol.
Version 2: 384-well plates, Primary screen, C3H/10T1/2 cells.
Aim: to screen chemical libraries for potential Sonic Hedgehog pathway inhibitors.

Materials

C3H/10T1/2 cells, grown in DMEM medium/10% FBS to 75-90% confluent
Assay Plates: 384-well white wall tissue culture plates Corning product #3707
Dilution plates: 384 deep-well plates Greiner Bio-One product #781270
Tested compounds as 10 mM DMSO solutions in 96-tube racks, columns 1 and 12 DMSO only, 80 compounds per rack.
Recombinant Human Sonic Hedgehog (C24II) protein, RDS product #1845-SH, reconstituted at 200 μg/ml in PBS.
Lysis Buffer: 10 mM Ethanolamine Buffer (pH 8.0), 0.2% Triton-X100, supplemented 1:100 with Protease Inhibitor Cocktail (EMD Bioscience product #539134).
HBSS for compound dilution and cell washing, prepare 1× solution from 10× concentrate (Invitrogen product number 14185-052) and filter-sterilize.
CSPD Alkaline Phosphatase Substrate with Emerald-II (Applied Biosystems product #T2212).
Liquid Handling
Perform steps 1 and 2 using Hydra 96 instrument with a 4-quadrant plate positioner.

Perform step 5 using Matrix 8-channel automatic pipettor.
Perform steps 7 and 9 using Tomtec Quadra Plus liquid handler.

Procedure

Prepare Assay plates:
  a. Designate and label 2 parallel assay plates for every 4 96-tube racks with tested compounds
  b. Harvest C3H/10T1/2 cells with TrypLE Express solution according to a regular cell subculture protocol
  c. Count the cells and calculate dilution necessary to obtain cell suspension at $1 \times 10^3$ cells per 24 μl ($4.17 \times 10^5$ cells/ml)
  d. Dilute cells with DMEM/10% FBS and distribute at 24 μl/well
  e. Place the plates into the incubator let grow overnight.

Compound dilution and addition:
  a. Designate and label 1 dilution plate for every 4 96-tube racks with tested compounds.
  b. Add 198 μl of HBSS per well to the dilution plate(s).
  c. Add 2 μl from compound library rack 1 to the dilution plate wells in quadrant 1 and run 2 mix cycles. This yields 100 μM intermediate compound dilutions.
  d. Transfer 3 μl of compound solutions from dilution plate quadrant 1 to the wells in quadrant 1 of the 2 parallel assay plates.
  e. Repeat steps 2.c-2.e for compound library racks 2 to 4 using corresponding quadrants 2 to 4 in dilution and assay plates, 3. Place plates into incubator for 20-30 min.
4. Prepare 3 μg/ml 10× solution of Sonic Hedgehog (C2411) protein (Hh) in DMEM/10% FBS:
  a. Calculate total volume needed as 1.2 ml per each assay plate.
  b. Add 15 μl of Hh stock solution (200 μg/ml in PBS) per each 985 μl of growth medium
5. Add 3 μl/well of 10× Hh solution to the wells columns 3-24. Use 125 μl automatic repeating pipettor. Add 3 μl/well of Growth medium to the negative control columns 1 and 2
6. Place plates into incubator for 4 days.
7. Run "Hh Add Lysis Buffer" program on Tomtec Quadra plus instrument. The instrument will:
  a. Wash cells on plate: aspirate medium, add 40 μl/well of HBSS and aspirate again.
  b. Add 7.5 μl/well of lysis buffer
8. Transfer plate(s) to the shaker platform and incubate for 15 min. at room temperature.
9. Run "Hh Add AP Substrate" program on Tomtec Quadra plus instrument. The instrument will:
  a. Add 45 μl/well of CSPD Alkaline Phosphatase substrate.
  b. Mix twice
10. Cover from light and incubate for 45 min. at room temperature on a shaker platform.
11. Read the plate(s) on Wallac VictorV reader using Luminescence (0.1 s) 384 protocol.

Calculations

Calculate %Inhibition=$((L^{DMSO}-L^{Cpd})/(L^{DMSO}-L^{neg}))\times 100$

Where
  $L^{Cpd}$ is luminescence in a well with tested compound;
  $L^{DMSO}$ is average luminescence in wells A23-P23 corresponding to positive control cells treated with DMSO and Hedgehog;
  $L^{neg}$ is average luminescence in wells A2-P2 corresponding to negative control cells treated with DMSO only.

EXAMPLES

Below the invention is described by means of specific examples, which illustrate but not limit the scope of the invention.

Starting Reagents And Physical-Chemical Methods of Confirmation of Structure And Purity of Synthesized Compounds All solvents and reagents used were received from commercial sources, such as Acros (Belgium), Sigma-Aldrich (USA), Lancaster (England) and ChemDiv (USA). Melting points were determined with instrument Buchi (Switzerland) model B-520. $^1$H and $^{13}$C NMR spectra were measured with spectrometer Gemini-300 (300 MHz) (Varian) in CDCl$_3$, chemical shifts are given in δ (m.d.). Internal standard is tetramethylsilane.

The main content of the substance was checked by HPLC method with Shimadzu instrument 10-AV (colomn Luna-C18, Phenomenex, 25 cm×4.6 mm, UV detecting at 215 and 254 nm) and LCMS with Applied Biosystems instrument (Shimadzu 10-AV LC, Gilson-215 automatic delivery of the sample, mass spectrometer API 150EX, detectors UV (215 and 254 nm) and ELS, colomn Luna-C 18, Phenomenex, 5 cm×2 mm).

Analytical TLC was carried out using Silufol UV$_{254}$ (5 sm×15 sm) (Kavalier, Czech Republic) or on glass plates with 0.25 mm silicagel 60 F$_{254}$ (Merck, Germany) layer. Visualisation was performed by UV light at 254 nm. Silicagel 5-40 μm (Chemapol, Czech Republic) and 63 μm (EM Science, USA) were used for chromatographic purification of compounds. According to LCMS data all synthesized compounds were of 95% purity.

Biological Tests And Activity of Synthesized Compounds

Example 1

Screening of the Library of the Compounds

Cells C3H10T1/2 were used for identification of inhibitors of SHh-protein signaling cascade. SHh-protein activates cells C3H10T1/2, that leads to their osteogenic differentiation [1] Kinto N., Iwamoto M., Enomoto-Iwamoto M., Noji S., Ohuchi H., Yoshioka H., Kataoka H., Wada Y., Yuhao G., Takahashi H. E., Yoshiki S., Yamaguchi A. Fibroblasts expressing Sonic hedgehog induce osteoblast differentiation and ectopic bone formation. *FEBS Lett.* 1997; 404 (2-3): 319-23. 2) Spinella-Jaegle S., Rawadi G., Kawai S., Gallea S., Faucheu C., Mollat P., Courtois B., Bergaud B., Ramez V., Blanchet A. M., Adelmant G., Baron R., Roman-Roman S. Sonic hedgehog increases the commitment of pluripotent mesenchymal cells into the osteoblastic lineage and abolishes adipocytic differentiation. *J. Cell Sci.* 2001; 114 (Pt 11): 2085-94] and, in particular, to expression enhancement of alkaline phosphatase enzyme.

The cells were cultivated in DMEM medium with 10% embryonal calfish serum in incubator at 37° C., 100% humidity and 5% CO$_2$ content. The cells were placed in 384-well plates and left for a night. On the next day the tested compounds in concentration of 10 μM were added to the cells, incubated for 30 min, then recombinant (R & D Systems, USA) SHh protein in concentration of 0.3 µg/ml was added and incubation was continued for 3 days. Cells together with DMSO instead of testable compound and cells without SHh protein were used as test controls. For determination of the cell alkaline phosphatase activity the cells were lysed in buffer containing 0.2% Triton-X100, lisates were incubated together with proluminescent substrate CSPD (Applied Biosystems, USA) and measured luminescence using reader VICTOR²V (PerkinElmer, USA).

For elimination of compounds nonspecifically inhibiting alkaline phosphatase the cells were primarily incubated with SHh protein for 3 days, lysed and before determination of alkaline phosphatase activity the tested compounds were added. For elimination of cytotoxic compounds the cells were incubated together with the tested compounds and SHh proteins for 3 days and the amount of living cells in the corresponding well using reagent CellTiter-Blue (Promega, USA).

Example 2

Determination of Inhibiting Activity (IC50)

The ability of the compounds to inhibit Hh-signalling cascade was determined using cells C3H10T1/2 in 384-well plates. The compounds were added in triplicates in various concentrations, prepared by multiple dilution of starting solutions. Activity of the compounds was determined by the concentration of the compounds causing half maximal inhibition of stimulation of cell alkaline phosphatase SHh ($IC_{50}$). Activity values for some inhibitors are represented in Table 1.

Inhibiting activity of the compounds given in Table 1 is represented in the following way:

A—$IC_{50}$: <500 nM; B—$IC_{50}$: <5.0 µl M; C—$IC_{50}$: <50 µM; D—$IC_{50}$: >50 µM

TABLE 1

Examples of compounds tested

| No. | Structure | Data | Activity |
|---|---|---|---|
| Cpd-001 | 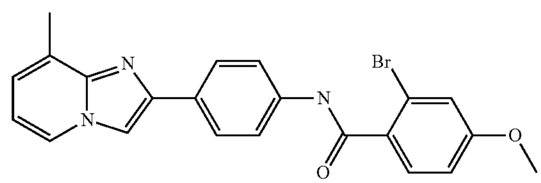 [SMILES: COc1ccc(C(=O)Nc2ccc(-c3cn4cccc(C)c4n3)cc2)c(Br)c1] | ¹HNMR (DMSO-d6): δ 10.44(s, 1H), 8.36 (d, 1H), 8.31(s, 1H), 7.95(d, 2H), 7.80(d, 2H), 7.53(d, 1H), 7.28(s, 1H), 7.04(m, 2H), 6.78(m, 1H), 3.83(s, 3H), 2.53(s, 3H). | A |
| Cpd-002 | 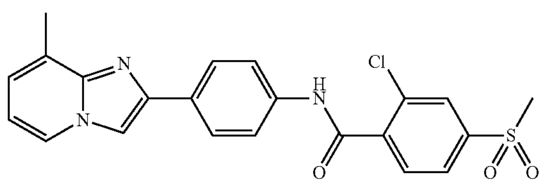 [SMILES: Cc1cccn2cc(-c3ccc(NC(=O)c4ccc(S(C)(=O)=O)cc4Cl)cc3)nc12] | ¹HNMR (DMSO-d6): δ 10.90(s, 1H), 8.61 (m, 3H), 8.05(m, 3H), 7.84-7.90(m, 3H), 7.57(d, 1H), 7.25(m, 1H), 3.40(s, 3H), 2.63(s, 3H) 2.63(s, 3H) | A |
| Cpd-003 | 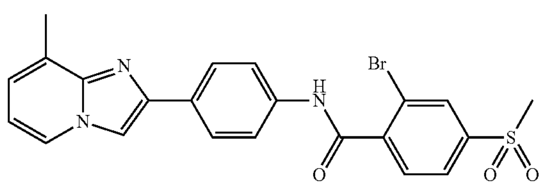 [SMILES: Cc1cccn2cc(-c3ccc(NC(=O)c4ccc(S(C)(=O)=O)cc4Br)cc3)nc12] | ¹HNMR (DMSO-d6): δ 10.92(s, 1H), 8.63 (m, 2H), 8.27(s, 1H), 7.98-8.10(m, 3H), 7.85-7.93(m, 3H), 7.58(d, 1H), 7.26(m, 1H), 3.36(s, 3H), 2.63(s, 3H) | A |
| Cpd-004 | 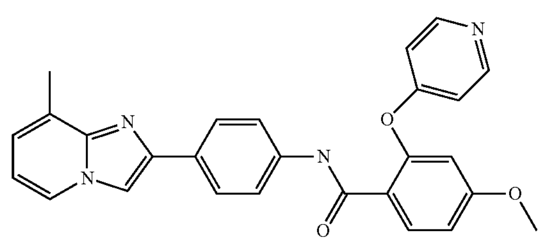 [SMILES: COc1ccc(C(=O)Nc2ccc(-c3cn4cccc(C)c4n3)cc2)c(Oc2ccncc2)c1] | ¹HNMR (DMSO-d6): δ 10.21(s, 1H), 8.61 (m, 3H), 8.57(d, 1H), 8.02(d, 2H), 7.40-7.47(m, 5H), 7.348(d, 1H), 7.15(m, 1H), 6.398(dd, 1H), 6.23(d, 1H), 3.66(s, 3H), 2.59(s, 3H). | B |
| Cpd-005 | 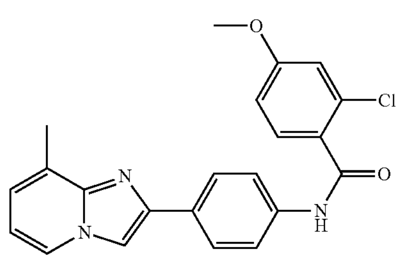 [SMILES: COc1ccc(C(=O)Nc2ccc(-c3cn4cccc(C)c4n3)cc2)c(Cl)c1] | ¹HNMR (DMSO-d6): δ 10.43(s, 1H), 8.37 (d, 1H), 8.32(s, 1H), 7.93(d, 2H), 7.80(d, 2H), 7.54(d, 1H), 7.13(s, 1H), 7.04(m, 2H), 6.79(t, 1H), 3.84(s, 3H), 2.53(s, 3H) | A |

TABLE 1-continued

Examples of compounds tested

| No. | Structure | Data | Activity |
| --- | --- | --- | --- |
| Cpd-006 | 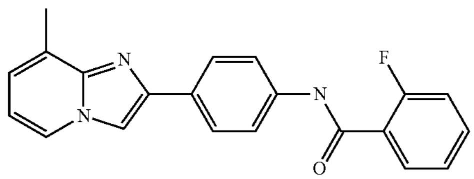 [SMILES: Cc1cccn2cc(-c3ccc(NC(=O)c4ccccc4F)cc3)nc12] | ¹HNMR (DMSO-d6): δ 10.30(s, 1H), 8.32 (d, 1H), 8.23(s, 1H), 7.91(d, 2H), 7.80(d, 2H), 7.67(t, 1H), 7.56(m, 1H), 7.36-7.32 (m, 2H), 6.97(d, 1H), 6.73(t, 1H), 2.56(s, 3H) | B |
| Cpd-007 | 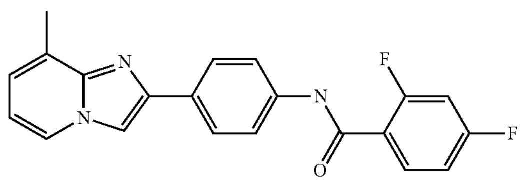 [SMILES: Cc1cccn2cc(-c3ccc(NC(=O)c4ccc(F)cc4F)cc3)nc12] | LSMS MW(+1) 364 | C |
| Cpd-008 | 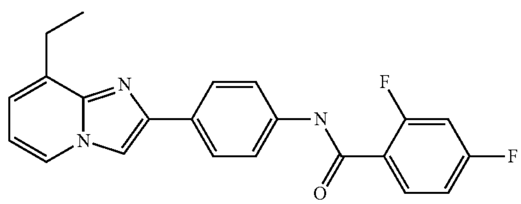 [SMILES: CCc1cccn2cc(-c3ccc(NC(=O)c4ccc(F)cc4F)cc3)nc12] | LSMS MW(+1) 378 | B |
| Cpd-009 | 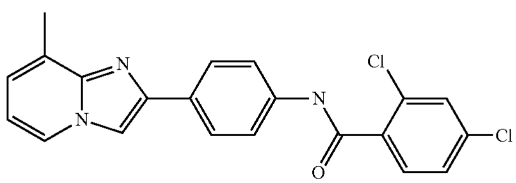 [SMILES: Cc1cccn2cc(-c3ccc(NC(=O)c4ccc(Cl)cc4Cl)cc3)nc12] | LSMS MW(+1) 396 | C |
| Cpd-010 | 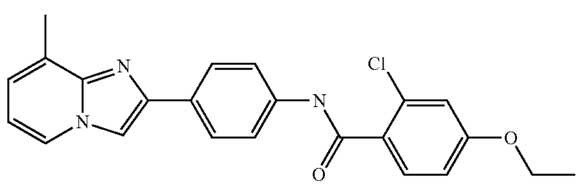 [SMILES: CCOc1ccc(C(=O)Nc2ccc(-c3cn4cccc(C)c4n3)cc2)c(Cl)c1] | LSMS MW(+1) 406 | A |
| Cpd-011 | 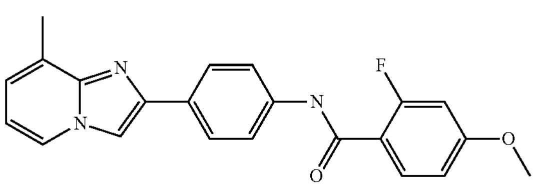 [SMILES: COc1ccc(C(=O)Nc2ccc(-c3cn4cccc(C)c4n3)cc2)c(F)c1] | LSMS MW(+1) 376 | A |
| Cpd-012 | 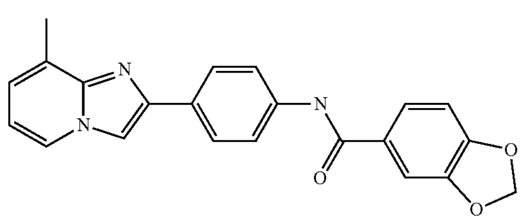 [SMILES: Cc1cccn2cc(-c3ccc(NC(=O)c4ccc5c(c4)OCO5)cc3)nc12] | LSMS MW(+1) 372 | B |

TABLE 1-continued

Examples of compounds tested

| No. | Structure | Data | Activity |
|---|---|---|---|
| Cpd-013 | 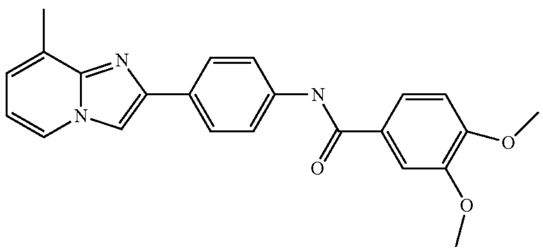 [SMILES: COc1ccc(C(=O)Nc2ccc(-c3cn4cccc(C)c4n3)cc2)cc1OC] | LSMS MW(+1) 388 | A |
| Cpd-014 | 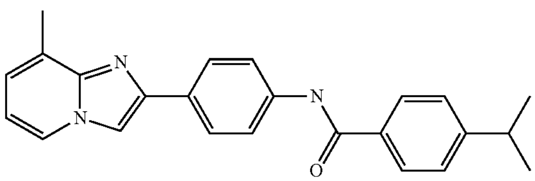 [SMILES: Cc1cccn2cc(-c3ccc(NC(=O)c4ccc(C(C)C)cc4)cc3)nc12] | LSMS MW(+1) 370 | C |
| Cpd-015 | 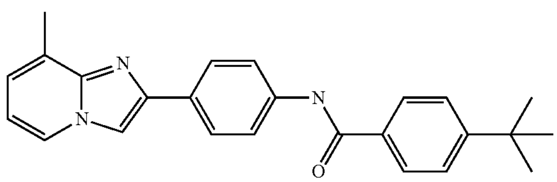 [SMILES: Cc1cccn2cc(-c3ccc(NC(=O)c4ccc(C(C)(C)C)cc4)cc3)nc12] | LSMS MW(+1) 384 | B |
| Cpd-016 | 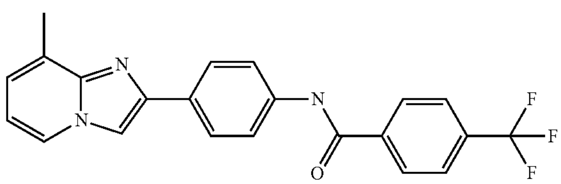 [SMILES: Cc1cccn2cc(-c3ccc(NC(=O)c4ccc(C(F)(F)F)cc4)cc3)nc12] | LSMS MW(+1) 396 | D |
| Cpd-017 | 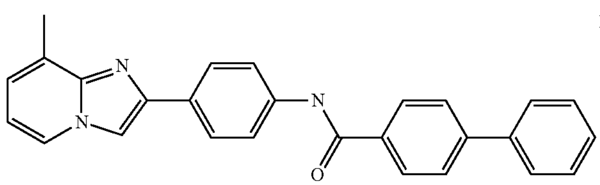 [SMILES: Cc1cccn2cc(-c3ccc(NC(=O)c4ccc(-c5ccccc5)cc4)cc3)nc12] | LSMS MW(+1) 404 | C |
| Cpd-018 | 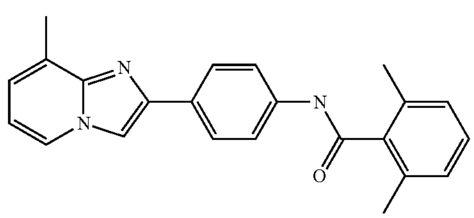 [SMILES: Cc1cccc(C)c1C(=O)Nc1ccc(-c2cn3cccc(C)c3n2)cc1] | LSMS MW(+1) 356 | A |
| Cpd-019 | 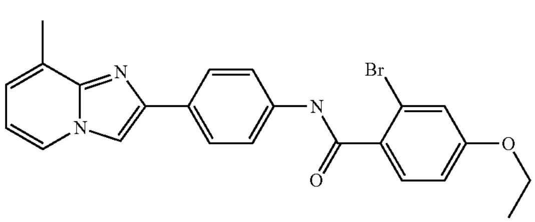 [SMILES: CCOc1ccc(C(=O)Nc2ccc(-c3cn4cccc(C)c4n3)cc2)c(Br)c1] | LSMS MW(+1) 451 | B |

TABLE 1-continued

Examples of compounds tested

| No. | Structure | Data | Activity |
|---|---|---|---|
| Cpd-020 | 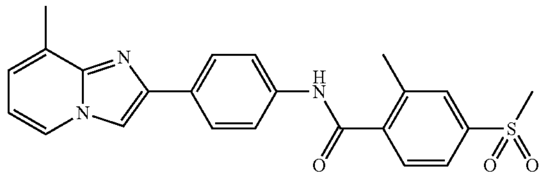 [SMILES: Cc1cc(S(C)(=O)=O)ccc1C(=O)Nc1ccc(-c2cn3cccc(C)c3n2)cc1] | LSMS MW(+1) 420 | A |

Example 3

Synthesis of the Compounds of the General Formula III

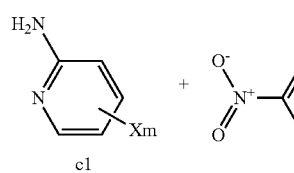
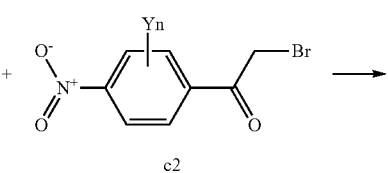

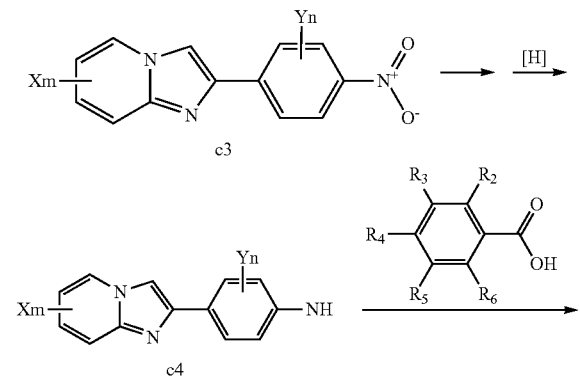

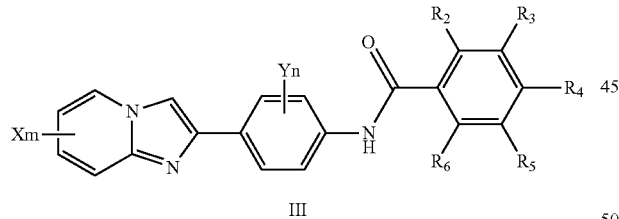

Compounds c3.

The mixture of aminopyridine c1 (0.04 mol) and nitrobromoacetophenone c2 (0.04 mol) in ethanol (80 ml) was boiled for 3 hours, then cooled to room temperature. The precipitate formed was filtered off, washed and dried in the opened air. Pure, yellow, crystalline product c3 was prepared with 66-75% yield.

Compounds c4.

Mixture of compound 3 (0.05 mol), $SnCl_2$ (0.18 mol), water (60 ml) and hydrochloric acid (80 ml) was stirred at 60° C. for 1 hour, then cooled to room temperature and poured into water (500 ml). The resultant mixture was basified with 10% solution of soda to pH 9-10. The precipitate formed was filtered off, washed with water, dried in the opened air and recrystallized from ethanol, that gave pure compound c4 as white crystals. The yield of compounds c4 is 75-88%.

Compounds of the General Formula III.

Carboxylic acid (1.1 mmol) was added to the solution of 1,1'-carbonyldiimidazole (1.2 mmol) in absolute DMF (5 ml). The reaction mixture was stirred at 80° C. for 1 hour without air access. Then primary or secondary amine (1 mmol) was added and the resultant reaction mixture was stirred at 100° C. for additional 3-4 hours and left for a night at room temperature. After that the reaction mixture was poured into 10-fold volume of water, the precipitate formed was filtered off, washed with water and dried in the opened air. Pure compounds of the general formula III were prepared by recrystallization from isopropanol, yield 30-75%, some of them are represented in Table 1.

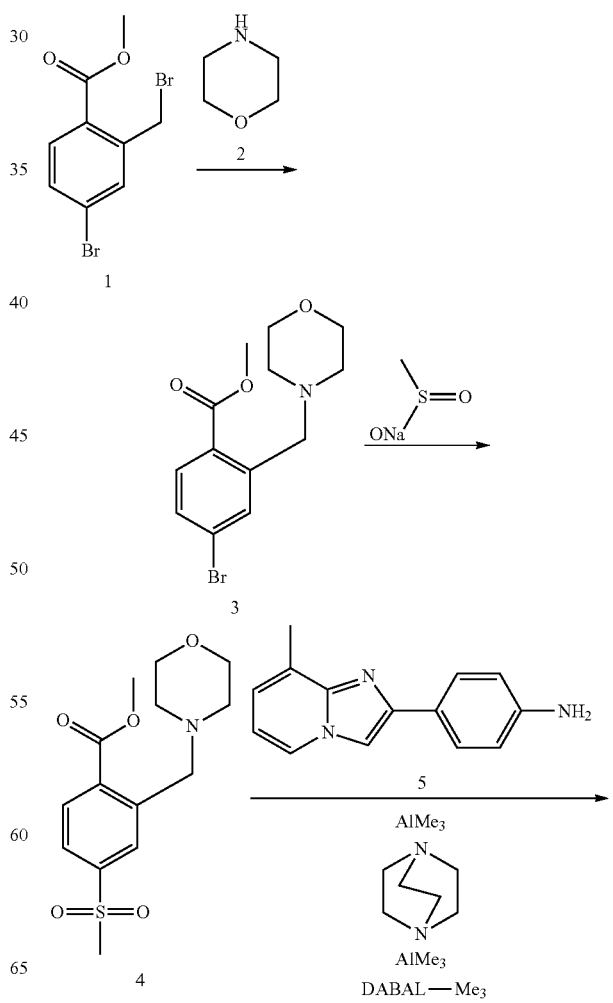

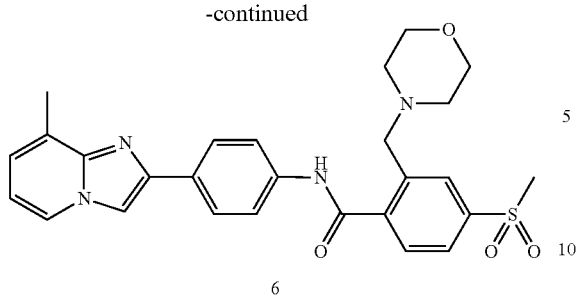

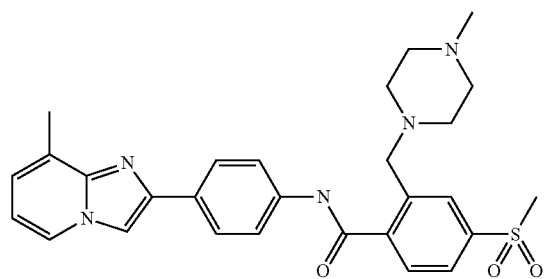

Yield 37%. ¹HNMR (DMSO-d6): δ 10.78 (s, 1H), 8.69 (m, 2H), 7.98-8.06 (m, 4H), 7.94 (d, 2H), 7.83 (d, 1H), 7.69 (d, 1H), 7.35 (m, 1H), 3.83 (s, 2H), 3.30-3.40 (m, 2H), 3.28 (s, 3H), 2.70-2.90 (m, 6H), 2.67 (s, 3H), 2.65 (s, 3H).

Example 4

General Procedure for Aminaton of Benzyl Bromides.

Benzyl bromide 1 (0.5 g, 1.93 mmol) refluxed with amine 2 (0.39 g, 3.86 mmol, 2 eq) in 20 ml THF for 4 hours. The reaction mixture was cooled, and precipitate was filtered off. Concentration in vacuo of the mother liquor gave product 3. Yield is quantitative.

General Procedure for CuI-Catalyzed Coupling of Aryl Halides and Sodium Methanesulfunate.

A mixture of aryl halide 3 (1 mmol), sodium methanesulfunate (1.2 mmol), copper iodide (0.1 mmol), 1-proline sodium salt (0.2 mmol), and 2 mL of DMSO in a sealed tube was heated to 80 or 95° C. under argon. The cooled mixture was partitioned between ethyl acetate and water. The organic layer was separated, and the aqueous layer was extracted with ethyl acetate twice. The combined organic layers were washed with brine, dried over MgSO4, and concentrated in vacuo. The residual oil was loaded on a silica gel column and eluted with CHCl$_3$/MeOH to afford the product 4. Yield 30-50%

General Procedure for amide bond formation using DABAL-Me$_3$.

To a stirred solution of DABAL-Me$_3$ (1.44 mmol) in anhydrous THF (30 mL) under an inert atmosphere, aryl amine (1.15 mmol) was added. The solution was stirred and warmed to 40 C for 1 h. To this methyl benzoate (0.96 mmol) was added and the solution was refluxed for 18 h. The reaction mixture was cooled to ambient temperature and quenched with H$_2$O (20 ml) dropwise, followed by extraction with ethyl acetate (4*10 mL). The organic phase was separated and filtered through a small plug of silica. Removal of the solvent under reduced pressure gave amide. Purificated by HPLC if it is necessary.

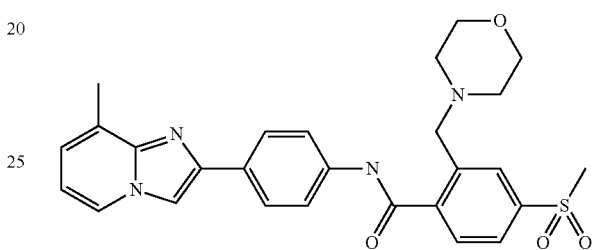

Yield 23%. ¹HNMR (DMSO-d6): δ 10.99 (s, 1H), 8.66 (m, 2H), 8.14-8.27 (m, 2H), 8.07-8.02 (m, 3H), 7.95 (d, 2H), 7.64 (d, 1H), 7.31 (m, 1H), 4.40 (br s, 2H), 3.90-3.80 (m, 4H), 3.32 (s, 3H), 3.02-3.23 (m, 4H), 2.64 (s, 3H).

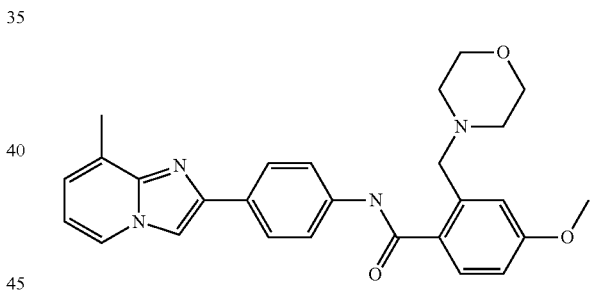

Yield 26%. ¹HNMR (DMSO-d6): δ 10.30 (s, 1H), 8.60 (s, 1H), 8.06 (d, 2H), 7.95 (d, 1H), 7.83 (d, 2H), 7.70 (d, 1H), 7.60 (d, 1H), 7.50 (s, 1H), 7.35 (d, 1H), 7.29 (m, 1H) 3.82 (s, 2H), 3.74 (s, 3H), 3.68 (m, 4H), 2.71 (m, 4H), 2.60 (s, 3H).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

All publications and patent applications mentioned in this specification are herein incorporated by reference to the same extent as if each individual publication or patent application was specifically and individually indicated to be incorporated by reference.

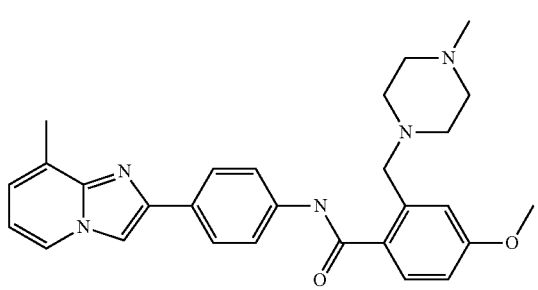 [SMILES: COc1ccc(C(=O)Nc2ccc(-c3cn4cccc(C)c4n3)cc2)c(CN2CCN(C)CC2)c1]

Yield 25%. ¹HNMR (DMSO-d6): δ 10.25 (s, 1H), 8.57 (s, 1H), 8.03 (d, 2H), 7.90 (d, 1H), 7.79 (d, 2H), 7.67 (d, 1H), 7.58 (d, 1H), 7.45 (s, 1H), 7.31 (d, 1H), 7.23 (m, 1H) 3.82 (s, 2H), 3.72 (s, 3H), 3.25-3.34 (m, 2H), 2.71-2.93 (m, 6H), 2.68 (s, 3H), 2.60 (s, 3H)

We claim:
1. A compound having the structure of Formula (I):

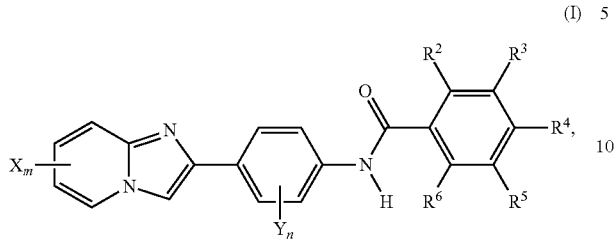

or a stereoisomer, hydrate, solvate or pharmaceutically acceptable salt thereof, wherein:

m is 1 or 2; n is 0, 1, or 2;
X is $C_1$-$C_3$ alkyl, halogen or CN;
Y is $C_1$-$C_3$ alkyl, halogen or CN;
$R^2$ is selected from the group consisting of Cl, Br, —CN, alkyl, —O-aryl, —O-heteroaryl, —CH$_2$-aryl, —CH$_2$-heteroaryl, —NH-aryl, —SO$_2$-aryl, —NH-heteroaryl, —NH-alkyl, —CH$_2$—NH-alkyl, —CH$_2$—N(alkyl)$_2$, —CH$_2$—(N-linked heterocycle), —CH$_2$—(C-linked heterocycle), N-linked heterocycle, and C-linked heterocycle;
$R^3$, $R^5$, and $R^6$ are independently selected from the group consisting of hydrogen, Cl, Br, —CN, alkyl, aryl, heteroaryl, C-linked heterocycle, —O-alkyl, —O-aryl, —O-heteroaryl, N-linked heterocycle, —NHalkyl, —N(alkyl)$_2$, —NHaryl, —NH-heteroaryl, —CO$_2$H, —CO$_2$alkyl, —SO$_2$alkyl, —SO$_2$NH$_2$, —SO$_2$NHalkyl, —SO$_2$N(alkyl)$_2$, —NHSO$_2$alkyl, —NHSO$_2$aryl, —NHCONHalkyl, —NHCON(alkyl)$_2$, —N(alkyl)CONH$_2$, —N(alkyl)CONH(alkyl), and —N(alkyl)CON(alkyl)$_2$; and
$R^4$ is selected from the group consisting of alkoxy, —CN, —SO$_2$-alkyl, —SO$_2$NH$_2$, —SO$_2$NH-alkyl, —NHSO$_2$-alkyl, —NHSO$_2$-aryl, —NHCO-alkyl, —NHCO-aryl, —NHCONH-alkyl, —NHCONH-aryl, —CONH$_2$, —CONH-alkyl, —CONH-aryl, —CON(alkyl)$_2$, —CON(aryl)$_2$, —CO$_2$H, and —CO$_2$alkyl.

2. The compound of claim 1, wherein n is 0 or 1, and m is 1.
3. The compound of claim 2, wherein X is $C_1$-$C_3$ alkyl.
4. The compound of claim 3 having the structure of Formula (II):

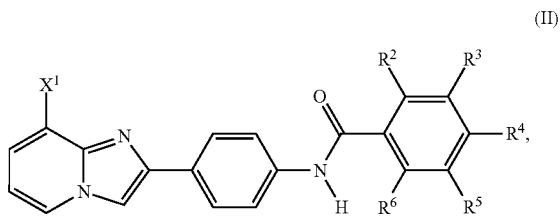

or a stereoisomer, hydrate, solvate or pharmaceutically acceptable salt thereof, wherein:
$X^1$ is $C_1$-$C_3$ alkyl;
$R^2$ is selected from the group consisting of Cl, Br, —CN, alkyl, —O-aryl, —O-heteroaryl, —CH$_2$-aryl, —CH$_2$-heteroaryl, —NH-aryl, —NH-heteroaryl, —NH-alkyl, —CH$_2$—NH-alkyl, —CH$_2$—N(alkyl)$_2$, —CH$_2$—(N-linked heterocycle), —CH$_2$—(C-linked heterocycle), N-linked heterocycle, and C-linked heterocycle;
$R^3$, $R^5$, and $R^6$ are independently selected from the group consisting of hydrogen, Cl, Br, —CN, alkyl, aryl, heteroaryl, C-linked heterocycle, —O-alkyl, —O-aryl, —O-heteroaryl, N-linked heterocycle, —NHalkyl, —N(alkyl)$_2$, —NHaryl, —NH-heteroaryl, —CO$_2$H, —CO$_2$alkyl, —SO$_2$alkyl, —SO$_2$NH$_2$, —SO$_2$NHalkyl, —SO$_2$N(alkyl)$_2$, —NHSO$_2$alkyl, —NHSO$_2$aryl, —NHCONHalkyl, —NHCON(alkyl)$_2$, —N(alkyl)CONH$_2$, —N(alkyl)CONH(alkyl), and —N(alkyl)CON(alkyl)$_2$; and
$R^4$ is selected from the group consisting of alkoxy, —CN, —SO$_2$-alkyl, —SO$_2$NH$_2$, —SO$_2$NH-alkyl, —NHSO$_2$-alkyl, —NHSO$_2$-aryl, —NHCO-alkyl, —NHCO-aryl, —NHCONH-alkyl, —NHCONH-aryl, —CONH$_2$, —CONH-alkyl, —CONH-aryl, —CON(alkyl)$_2$, —CON(aryl)$_2$, —CO$_2$H, and —CO$_2$alkyl.

5. The compound of claim 4, wherein
$R^2$ is selected from the group consisting of Cl, Br, —CN, alkyl, —O-aryl, —O-heteroaryl, —CH$_2$-aryl, —CH$_2$-heteroaryl, —NH-aryl, —NH-heteroaryl, —NH-alkyl, —CH$_2$—NH-alkyl, —CH$_2$—N(alkyl)$_2$, —CH$_2$—(N-linked heterocycle), —CH$_2$—(C-linked heterocycle), N-linked heterocycle, and C-linked heterocycle;
$R^3$, $R^5$, and $R^6$ are independently selected from the group consisting of hydrogen, Cl, Br, —CN, alkyl, aryl, heteroaryl, —O-alkyl, —CO$_2$H, —SO$_2$alkyl, —SO$_2$NH$_2$, —SO$_2$NHalkyl, —SO$_2$N(alkyl)$_2$, and —NHSO$_2$alkyl; and
$R^4$ is selected from the group consisting of alkoxy, —CN, —SO$_2$-alkyl, —SO$_2$NH$_2$, —SO$_2$NH-alkyl, —NHSO$_2$-alkyl, —NHSO$_2$-aryl, —NHCO-alkyl, —NHCO-aryl, —NHCONH-alkyl, —NHCONH-aryl, —CONH$_2$, —CONH-alkyl, —CONH-aryl, —CON(alkyl)$_2$, —CON(aryl)$_2$, —CO$_2$H, and —CO$_2$alkyl.

6. The compound of claim 5, wherein
$R^3$, $R^5$, and $R^6$ are independently selected from the group consisting of hydrogen, Cl, Br, —CN, alkyl, —O-alkyl, —CO$_2$H, —SO$_2$alkyl, and —SO$_2$NH$_2$.

7. The compound of claim 5, wherein
$R^4$ is selected from the group consisting of alkoxy, —CN, —SO$_2$-alkyl, —SO$_2$NH$_2$, —NHSO$_2$-alkyl, —CONH$_2$, —CONH-alkyl, and —CO$_2$H.

8. The compound of claim 5, wherein
$R^3$, $R^5$, and $R^6$ are independently selected from the group consisting of hydrogen, Cl, Br, —CN, alkyl, —O-alkyl, —CO$_2$H, —SO$_2$alkyl, and —SO$_2$NH$_2$; and
$R^4$ is selected from the group consisting of alkoxy, —CN, —SO$_2$-alkyl, —SO$_2$NH$_2$, —NHSO$_2$-alkyl, —CONH$_2$, —CONH-alkyl, and —CO$_2$H.

9. The compound of claim 8, wherein $X^1$ is methyl, ethyl, or trifluoromethyl.
10. The compound of claim 9, wherein $R^3$, $R^5$, and $R^6$ are hydrogen.
11. The compound of claim 9, wherein $R^4$ is selected from alkoxy or —SO$_2$-alkyl.
12. The compound of claim 9, wherein
$R^2$ is selected from the group consisting of Cl, Br, —CN,

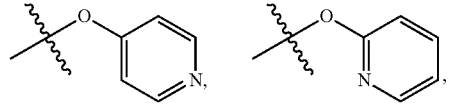

-continued
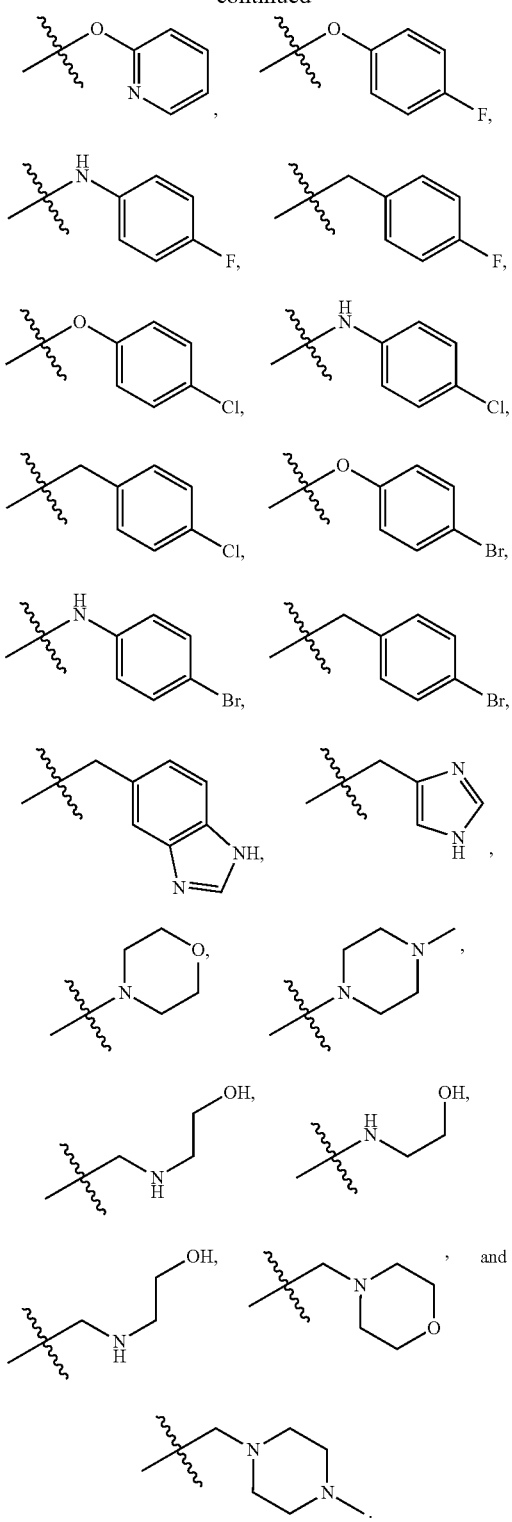
13. The compound of claim 12, wherein $R^3$, $R^5$, and $R^6$ are hydrogen.
14. The compound of claim 13, wherein $R^4$ is selected from alkoxy or —$SO_2$-alkyl.
15. The compound of claim 14, wherein $R^4$ is —$OCH_3$ or —$SO_2CH_3$.
16. A compound selected from the group consisting of:
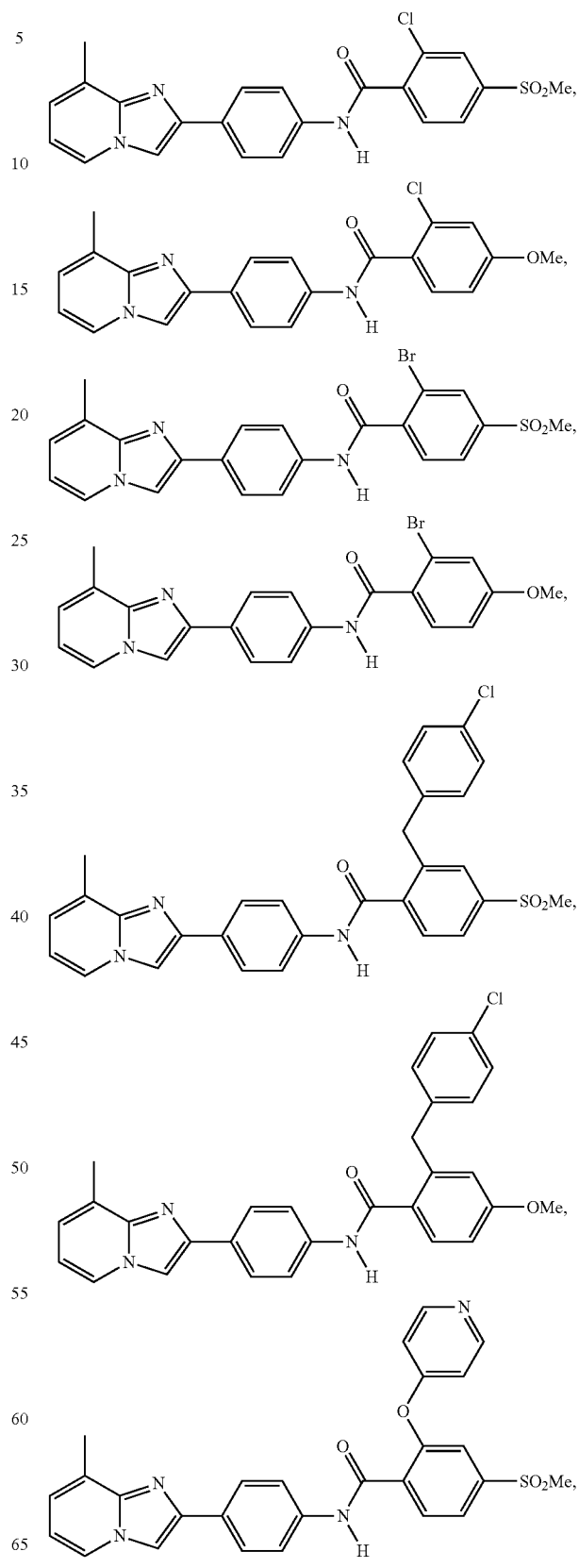

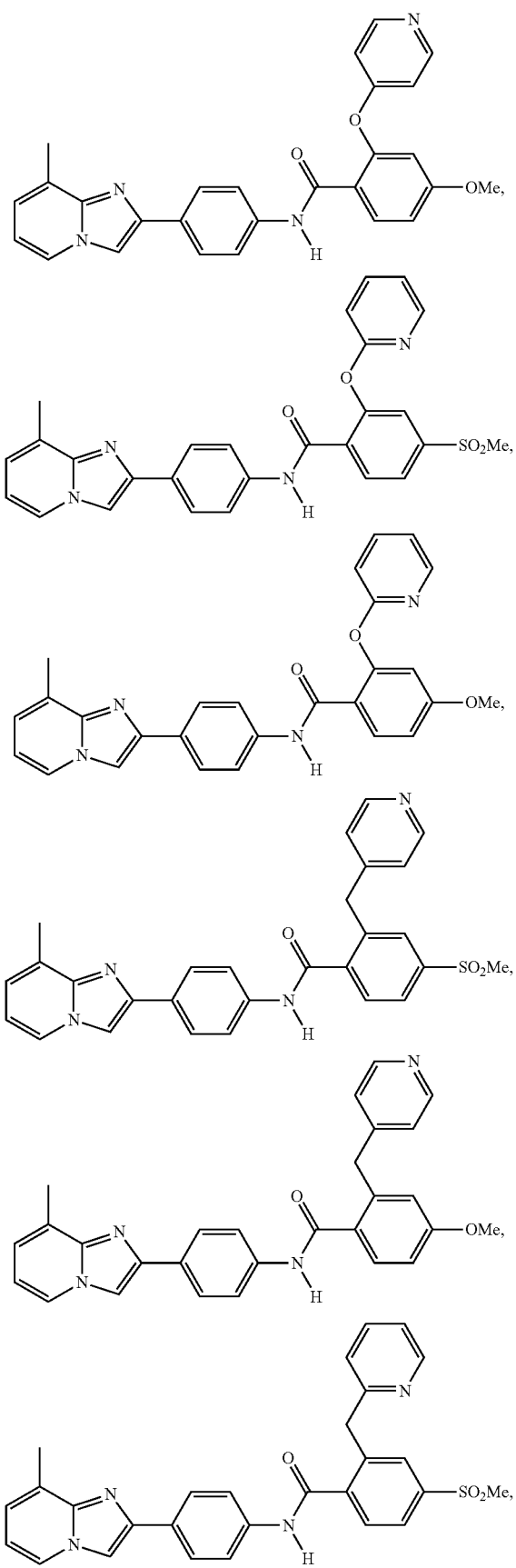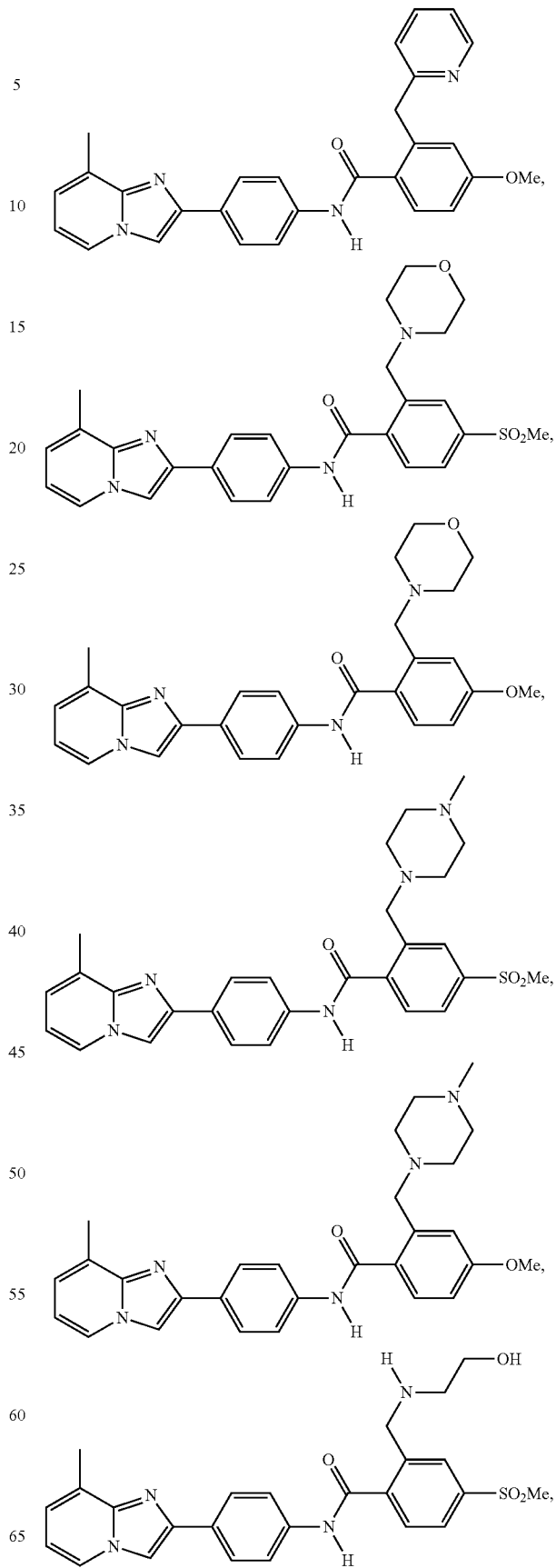

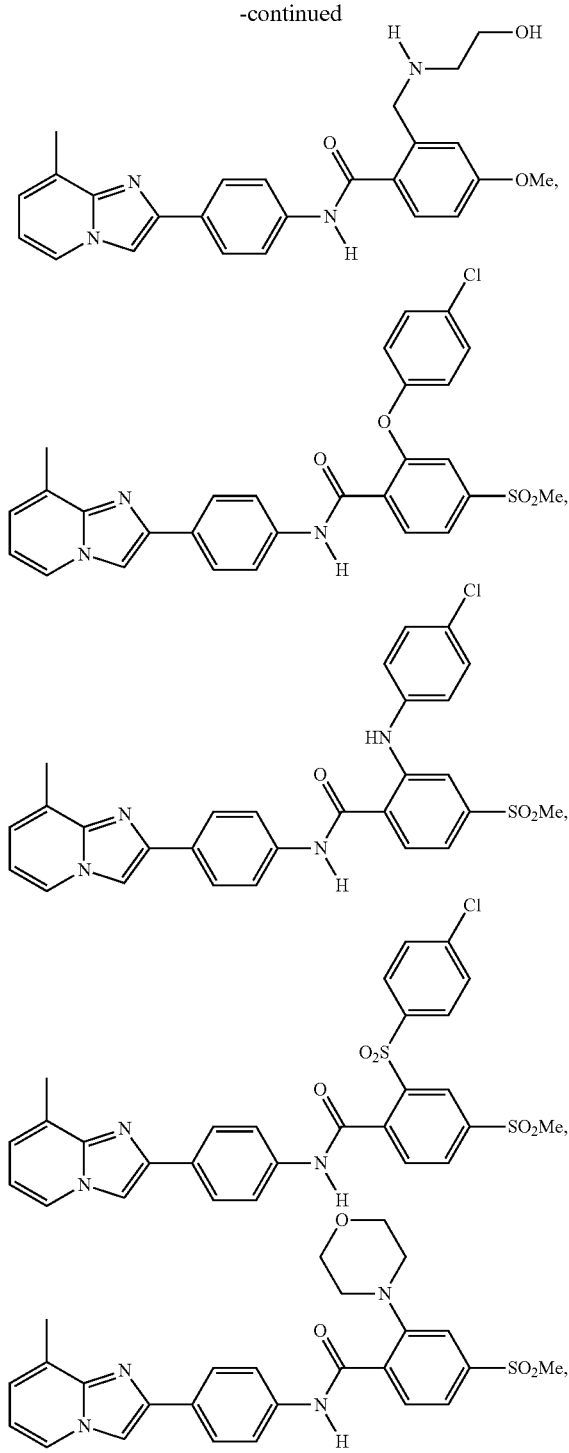
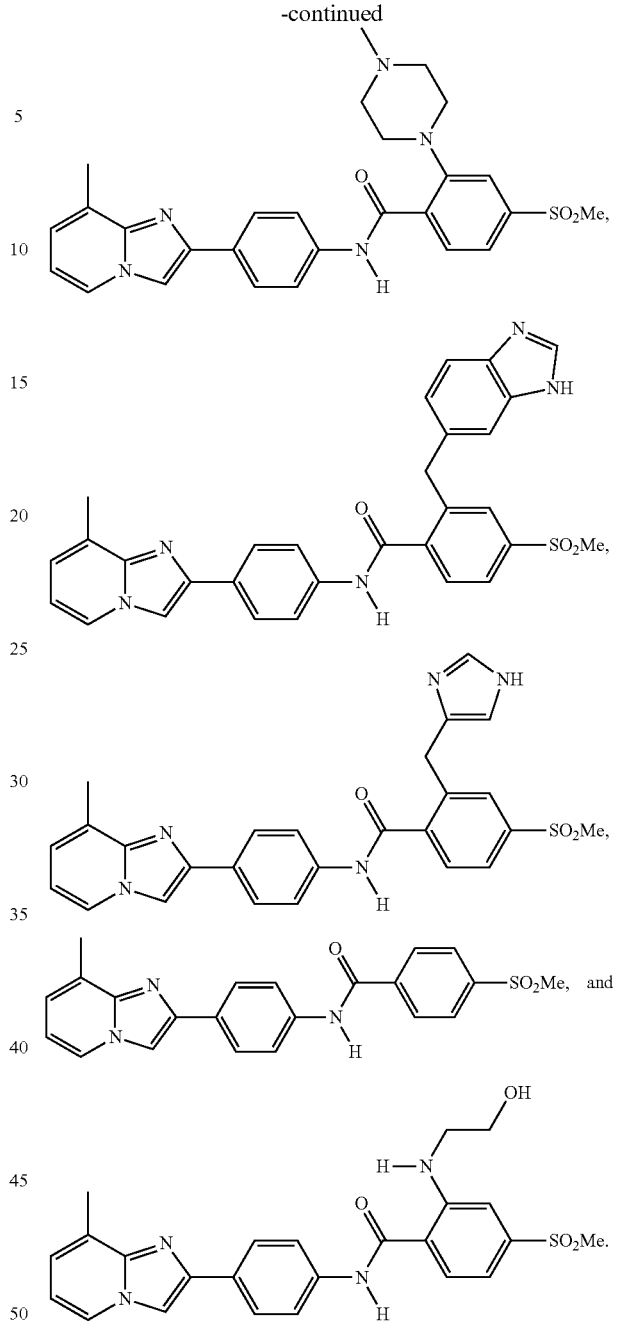
17. A pharmaceutical composition comprising a compound of claim 1 and at least one pharmaceutically acceptable excipient.
* * * * *